United States Patent
Desallais et al.

(10) Patent No.: US 10,456,456 B2
(45) Date of Patent: *Oct. 29, 2019

(54) ANTI-IL-6 VACCINE COMPOSITION

(71) Applicant: PEPTINOV SAS, Paris (FR)

(72) Inventors: Lucille Desallais, Paris (FR); Matthieu Montes, Paris (FR); Jean-Francois Zagury, Paris (FR)

(73) Assignee: PEPTINOV SAS, Paris (FR)

( * ) Notice: Subject to any disclaimer, the term of this patent is extended or adjusted under 35 U.S.C. 154(b) by 3 days.

This patent is subject to a terminal disclaimer.

(21) Appl. No.: 15/610,961

(22) Filed: Jun. 1, 2017

(65) Prior Publication Data

US 2017/0333539 A1 Nov. 23, 2017

Related U.S. Application Data

(63) Continuation of application No. 14/237,942, filed as application No. PCT/IB2012/001998 on Aug. 9, 2012, now Pat. No. 9,669,077.

(60) Provisional application No. 61/521,533, filed on Aug. 9, 2011.

(30) Foreign Application Priority Data

Aug. 9, 2011 (FR) .................... 11 57267

(51) Int. Cl.
*A61K 38/20* (2006.01)
*A61K 39/00* (2006.01)
*C07K 14/54* (2006.01)
*C12N 15/115* (2010.01)
*C07K 16/24* (2006.01)
*C07K 7/04* (2006.01)
*C07K 7/54* (2006.01)
*C07K 7/64* (2006.01)

(52) U.S. Cl.
CPC ........ *A61K 39/0005* (2013.01); *A61K 38/204* (2013.01); *A61K 39/0008* (2013.01); *C07K 7/04* (2013.01); *C07K 7/54* (2013.01); *C07K 7/64* (2013.01); *C07K 14/54* (2013.01); *C07K 14/5412* (2013.01); *C07K 16/248* (2013.01); *C12N 15/115* (2013.01); *C12N 2310/16* (2013.01)

(58) Field of Classification Search
CPC ..................................... A61K 38/12
See application file for complete search history.

(56) References Cited

U.S. PATENT DOCUMENTS 9,669,077 B2 * 6/2017 Desallais ........... C07K 14/5412
2010/0138945 A1 6/2010 Frey et al.

FOREIGN PATENT DOCUMENTS

WO 2009094172 A2 3/2009

OTHER PUBLICATIONS

"Interleukin-6 antagonist peptide" XP002678751, Database Geneseq Online (Aug. 1996).
"Human B-cell simulator 2 (BSF2) antagonist" XP002678750, Database Geneseq Online (Jan. 1991).
"Human B-cell simulator 2 (BSF2) antagonist" XP002678749, Database Geneseq Online (Jan. 1991).

* cited by examiner

*Primary Examiner* — Prema M Mertz
(74) *Attorney, Agent, or Firm* — Browdy and Neimark, PLLC

(57) ABSTRACT

The present invention relates to a pharmaceutical composition comprising, by way of active ingredient, at least one polypeptide comprising, or constituted by a sequence constituted by at least 8 contiguous amino acids and from at the most 30 contiguous amino acids chosen from within the interleukin-6 sequence and from at the most 30 contiguous amino acids chosen from within the complete IL-6 sequence.

5 Claims, 7 Drawing Sheets

Specification includes a Sequence Listing.

SEQUENCE LISTING

<160> NUMBER OF SEQ ID NOS: 61

<210> SEQ ID NO 1
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Human IL-6 portion

<400> SEQUENCE: 1

```
Gly Ile Ser Ala Leu Arg Lys Glu Thr Cys Asn Lys Ser Asn Met Cys
1               5                   10                  15

<210> SEQ ID NO 2
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Human IL-6 portion

<400> SEQUENCE: 2

Cys Glu Ser Ser Lys Glu Ala Leu Ala Glu Asn Asn Leu Asn Leu Pro
1               5                   10                  15

Lys

<210> SEQ ID NO 3
<211> LENGTH: 11
<212> TYPE: PRT
<213> ORGANISM: Artificial Sequence
<220> FEATURE:
<223> OTHER INFORMATION: Human IL-6 portion
<220> FEATURE:
<221> NAME/KEY: misc_feature
<223> OTHER INFORMATION: Synthetic

<400> SEQUENCE: 3

Cys Phe Gln Ser Gly Phe Asn Glu Glu Thr Cys
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Human IL-6 portion
<220> FEATURE:
<221> NAME/KEY: misc_feature
<223> OTHER INFORMATION: Synthetic

<400> SEQUENCE: 4

Glu Tyr Leu Gln Asn Arg Phe Glu Ser Ser Glu Glu Gln Ala Arg
1               5                   10                  15

<210> SEQ ID NO 5
<211> LENGTH: 13
<212> TYPE: PRT
<213> ORGANISM: Artificial Sequence
<220> FEATURE:
<223> OTHER INFORMATION: Human IL-6 portion
<220> FEATURE:
<221> NAME/KEY: misc_feature
<223> OTHER INFORMATION: Synthetic

<400> SEQUENCE: 5

Thr Lys Leu Gln Ala Gln Asn Gln Trp Leu Gln Asp Met
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Human IL-6 portion variant
<220> FEATURE:
<221> NAME/KEY: misc_feature
```

-continued

<223> OTHER INFORMATION: Synthetic

<400> SEQUENCE: 6

Glu Phe Leu Gln Asn Arg Phe Glu Ser Ser Glu Glu Gln Ala Arg
1               5                   10                  15

<210> SEQ ID NO 7
<211> LENGTH: 13
<212> TYPE: PRT
<213> ORGANISM: Artificial Sequence
<220> FEATURE:
<223> OTHER INFORMATION: Human IL-6 portion variant
<220> FEATURE:
<221> NAME/KEY: misc_feature
<223> OTHER INFORMATION: Synthetic

<400> SEQUENCE: 7

Thr Lys Cys Gln Ala Gln Asn Gln Trp Leu Gln Asp Met
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Human IL-6 portion variant
<220> FEATURE:
<221> NAME/KEY: misc_feature
<223> OTHER INFORMATION: Synthetic

<400> SEQUENCE: 8

Gly Ile Ser Ala Val Arg Lys Asp Thr Cys Asn Lys Ser Gln Met Cys
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Human IL-6 portion variant
<220> FEATURE:
<221> NAME/KEY: misc_feature
<223> OTHER INFORMATION: Synthetic

<400> SEQUENCE: 9

Cys Glu Ser Ser Lys Asp Ala Ile Ala Glu Asn Gln Leu Asn Leu Pro
1               5                   10                  15

Lys

<210> SEQ ID NO 10
<211> LENGTH: 11
<212> TYPE: PRT
<213> ORGANISM: Artificial Sequence
<220> FEATURE:
<223> OTHER INFORMATION: Human IL-6 portion variant
<220> FEATURE:
<221> NAME/KEY: misc_feature
<223> OTHER INFORMATION: Synthetic

<400> SEQUENCE: 10

Cys Phe Asn Ser Gly Phe Asn Glu Asp Thr Cys
1               5                   10

<210> SEQ ID NO 11
<211> LENGTH: 15
<212> TYPE: PRT
<213> ORGANISM: Artificial Sequence
<220> FEATURE:

<223> OTHER INFORMATION: Human IL-6 portion variant
<220> FEATURE:
<221> NAME/KEY: misc_feature
<223> OTHER INFORMATION: Synthetic

<400> SEQUENCE: 11

Glu Phe Leu Gln Asn Arg Phe Asp Ser Ser Asp Glu Asn Ala Arg
1               5                   10                  15

<210> SEQ ID NO 12
<211> LENGTH: 13
<212> TYPE: PRT
<213> ORGANISM: Artificial Sequence
<220> FEATURE:
<223> OTHER INFORMATION: Human IL-6 portion variant
<220> FEATURE:
<221> NAME/KEY: misc_feature
<223> OTHER INFORMATION: Synthetic

<400> SEQUENCE: 12

Thr Lys Cys Gln Ala Asn Gln Gln Trp Leu Gln Glu Met
1               5                   10

<210> SEQ ID NO 13
<211> LENGTH: 18
<212> TYPE: PRT
<213> ORGANISM: Artificial Sequence
<220> FEATURE:
<223> OTHER INFORMATION: Modified human IL-6 portion
<220> FEATURE:
<221> NAME/KEY: misc_feature
<223> OTHER INFORMATION: Synthetic

<400> SEQUENCE: 13

Cys Glu Ser Ser Lys Glu Ala Leu Ala Glu Asn Asn Leu Asn Leu Pro
1               5                   10                  15

Lys Cys

<210> SEQ ID NO 14
<211> LENGTH: 17
<212> TYPE: PRT
<213> ORGANISM: Artificial Sequence
<220> FEATURE:
<223> OTHER INFORMATION: Modified human IL-6 portion variant
<220> FEATURE:
<221> NAME/KEY: misc_feature
<223> OTHER INFORMATION: Synthetic

<400> SEQUENCE: 14

Cys Glu Phe Leu Gln Asn Arg Phe Glu Ser Ser Glu Glu Gln Ala Arg
1               5                   10                  15

Cys

<210> SEQ ID NO 15
<211> LENGTH: 14
<212> TYPE: PRT
<213> ORGANISM: Artificial Sequence
<220> FEATURE:
<223> OTHER INFORMATION: Modified human IL-6 portion variant
<220> FEATURE:
<221> NAME/KEY: misc_feature
<223> OTHER INFORMATION: Synthetic

<400> SEQUENCE: 15

Thr Lys Cys Gln Ala Gln Asn Gln Trp Leu Gln Asp Met Cys
1               5                   10

<210> SEQ ID NO 16
<211> LENGTH: 17
<212> TYPE: PRT
<213> ORGANISM: Artificial Sequence
<220> FEATURE:
<223> OTHER INFORMATION: Modified human IL-6 portion
<220> FEATURE:
<221> NAME/KEY: misc_feature
<223> OTHER INFORMATION: Synthetic

<400> SEQUENCE: 16

Tyr Gly Ile Ser Ala Leu Arg Lys Glu Thr Cys Asn Lys Ser Asn Met
1               5                   10                  15

Cys

<210> SEQ ID NO 17
<211> LENGTH: 19
<212> TYPE: PRT
<213> ORGANISM: Artificial Sequence
<220> FEATURE:
<223> OTHER INFORMATION: Modified human IL-6 portion
<220> FEATURE:
<221> NAME/KEY: misc_feature
<223> OTHER INFORMATION: Synthetic

<400> SEQUENCE: 17

Cys Glu Ser Ser Lys Glu Ala Leu Ala Glu Asn Asn Leu Asn Leu Pro
1               5                   10                  15

Lys Cys Tyr

<210> SEQ ID NO 18
<211> LENGTH: 18
<212> TYPE: PRT
<213> ORGANISM: Artificial Sequence
<220> FEATURE:
<223> OTHER INFORMATION: Modified human IL-6 portion variant
<220> FEATURE:
<221> NAME/KEY: misc_feature
<223> OTHER INFORMATION: Synthetic

<400> SEQUENCE: 18

Tyr Cys Glu Phe Leu Gln Asn Arg Phe Glu Ser Ser Glu Glu Gln Ala
1               5                   10                  15

Arg Cys

<210> SEQ ID NO 19
<211> LENGTH: 15
<212> TYPE: PRT
<213> ORGANISM: Artificial Sequence
<220> FEATURE:
<223> OTHER INFORMATION: Modified human IL-6 portion variant
<220> FEATURE:
<221> NAME/KEY: misc_feature
<223> OTHER INFORMATION: Synthetic

<400> SEQUENCE: 19

Thr Lys Cys Gln Ala Gln Asn Gln Trp Leu Gln Asp Met Cys Tyr
1               5                   10                  15

<210> SEQ ID NO 20
<211> LENGTH: 17
<212> TYPE: PRT
<213> ORGANISM: Artificial Sequence
<220> FEATURE:
<223> OTHER INFORMATION: Modified human IL-6 portion variant
<220> FEATURE:
<221> NAME/KEY: misc_feature
<223> OTHER INFORMATION: Synthetic

<400> SEQUENCE: 20

Tyr Gly Ile Ser Ala Val Arg Lys Asp Thr Cys Asn Lys Ser Gln Met
1               5                   10                  15

Cys

<210> SEQ ID NO 21
<211> LENGTH: 19
<212> TYPE: PRT
<213> ORGANISM: Artificial Sequence
<220> FEATURE:
<223> OTHER INFORMATION: Modified human IL-6 portion variant
<220> FEATURE:
<221> NAME/KEY: misc_feature
<223> OTHER INFORMATION: Synthetic

<400> SEQUENCE: 21

Cys Glu Ser Ser Lys Asp Ala Ile Ala Glu Asn Gln Leu Asn Leu Pro
1               5                   10                  15

Lys Cys Tyr

<210> SEQ ID NO 22
<211> LENGTH: 18
<212> TYPE: PRT
<213> ORGANISM: Artificial Sequence
<220> FEATURE:
<223> OTHER INFORMATION: Modified human IL-6 portion variant
<220> FEATURE:
<221> NAME/KEY: misc_feature
<223> OTHER INFORMATION: Synthetic

<400> SEQUENCE: 22

Tyr Cys Glu Phe Leu Gln Asn Arg Phe Asp Ser Ser Asp Glu Asn Ala
1               5                   10                  15

Arg Cys

<210> SEQ ID NO 23
<211> LENGTH: 15
<212> TYPE: PRT
<213> ORGANISM: Artificial sequence
<220> FEATURE:
<223> OTHER INFORMATION: Modified human IL-6 portion variant
<220> FEATURE:
<221> NAME/KEY: misc_feature
<223> OTHER INFORMATION: Synthetic

<400> SEQUENCE: 23

Thr Lys Cys Gln Ala Asn Gln Gln Trp Leu Gln Glu Met Cys Tyr
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Murine IL-6 portion
<220> FEATURE:
<221> NAME/KEY: misc_feature
<223> OTHER INFORMATION: Synthetic

<400> SEQUENCE: 24

Glu Ile Val Glu Met Arg Lys Glu Leu Cys Asn Gly Asn Ser Asp
1               5                   10                  15

<210> SEQ ID NO 25
<211> LENGTH: 17

```
<212> TYPE: PRT
<213> ORGANISM: Artificial Sequence
<220> FEATURE:
<223> OTHER INFORMATION: Murine IL-6 portion
<220> FEATURE:
<221> NAME/KEY: misc_feature
<223> OTHER INFORMATION: Synthetic

<400> SEQUENCE: 25

Cys Met Asn Asn Asp Asp Ala Leu Ala Glu Asn Asn Leu Lys Leu Pro
1               5                   10                  15

Glu

<210> SEQ ID NO 26
<211> LENGTH: 11
<212> TYPE: PRT
<213> ORGANISM: Artificial Sequence
<220> FEATURE:
<223> OTHER INFORMATION: Murine IL-6 portion
<220> FEATURE:
<221> NAME/KEY: misc_feature
<223> OTHER INFORMATION: Synthetic

<400> SEQUENCE: 26

Cys Tyr Gln Thr Gly Tyr Asn Gln Glu Ile Cys
1               5                   10

<210> SEQ ID NO 27
<211> LENGTH: 16
<212> TYPE: PRT
<213> ORGANISM: Artificial Sequence
<220> FEATURE:
<223> OTHER INFORMATION: Murine IL-6 portion variant
<220> FEATURE:
<221> NAME/KEY: misc_feature
<223> OTHER INFORMATION: Synthetic

<400> SEQUENCE: 27

Glu Phe Met Lys Asn Asn Leu Lys Asp Asn Lys Lys Asp Lys Ala Arg
1               5                   10                  15

<210> SEQ ID NO 28
<211> LENGTH: 13
<212> TYPE: PRT
<213> ORGANISM: Artificial Sequence
<220> FEATURE:
<223> OTHER INFORMATION: Murine IL-6 portion variant
<220> FEATURE:
<221> NAME/KEY: misc_feature
<223> OTHER INFORMATION: Synthetic

<400> SEQUENCE: 28

Asp Lys Cys Glu Ser Gln Lys Glu Trp Leu Arg Thr Lys
1               5                   10

<210> SEQ ID NO 29
<211> LENGTH: 17
<212> TYPE: PRT
<213> ORGANISM: Artificial Sequence
<220> FEATURE:
<223> OTHER INFORMATION: Modified murine IL-6 portion
<220> FEATURE:
<221> NAME/KEY: misc_feature
<223> OTHER INFORMATION: Synthetic

<400> SEQUENCE: 29

Tyr Glu Ile Val Glu Met Arg Lys Glu Leu Cys Asn Gly Asn Ser Asp
1               5                   10                  15
```

Cys

<210> SEQ ID NO 30
<211> LENGTH: 19
<212> TYPE: PRT
<213> ORGANISM: Artificial Sequence
<220> FEATURE:
<223> OTHER INFORMATION: Modified murine IL-6 portion
<220> FEATURE:
<221> NAME/KEY: misc_feature
<223> OTHER INFORMATION: Synthetic

<400> SEQUENCE: 30

Cys Met Asn Asn Asp Asp Ala Leu Ala Glu Asn Asn Leu Lys Leu Pro
1               5                   10                  15

Glu Cys Tyr

<210> SEQ ID NO 31
<211> LENGTH: 19
<212> TYPE: PRT
<213> ORGANISM: Artificial Sequence
<220> FEATURE:
<223> OTHER INFORMATION: Modified murine IL-6 portion variant
<220> FEATURE:
<221> NAME/KEY: misc_feature
<223> OTHER INFORMATION: Synthetic

<400> SEQUENCE: 31

Tyr Cys Glu Phe Met Lys Asn Asn Leu Lys Asp Asn Lys Lys Asp Lys
1               5                   10                  15

Ala Arg Cys

<210> SEQ ID NO 32
<211> LENGTH: 15
<212> TYPE: PRT
<213> ORGANISM: Artificial Sequence
<220> FEATURE:
<223> OTHER INFORMATION: Modified murine IL-6 portion variant
<220> FEATURE:
<221> NAME/KEY: misc_feature
<223> OTHER INFORMATION: Synthetic

<400> SEQUENCE: 32

Asp Lys Cys Glu Ser Gln Lys Glu Trp Leu Arg Thr Lys Cys Tyr
1               5                   10                  15

<210> SEQ ID NO 33
<211> LENGTH: 18
<212> TYPE: PRT
<213> ORGANISM: Artificial Sequence
<220> FEATURE:
<223> OTHER INFORMATION: Modified murine IL-6 portion
<220> FEATURE:
<221> NAME/KEY: misc_feature
<223> OTHER INFORMATION: Synthetic

<400> SEQUENCE: 33

Cys Asn Gln Glu Val Lys Asp Leu His Lys Ile Val Leu Pro Thr Pro
1               5                   10                  15

Cys Tyr

<210> SEQ ID NO 34
<211> LENGTH: 15
<212> TYPE: PRT
<213> ORGANISM: Artificial Sequence
<220> FEATURE:
<223> OTHER INFORMATION: Monkey IL-6 portion

```
<220> FEATURE:
<221> NAME/KEY: misc_feature
<223> OTHER INFORMATION: Synthetic

<400> SEQUENCE: 34

Gly Ile Ser Ala Leu Arg Lys Glu Thr Cys Asn Arg Ser Asn Met
1               5                   10                  15

<210> SEQ ID NO 35
<211> LENGTH: 17
<212> TYPE: PRT
<213> ORGANISM: Artificial Sequence
<220> FEATURE:
<223> OTHER INFORMATION: Monkey IL-6 portion
<220> FEATURE:
<221> NAME/KEY: misc_feature
<223> OTHER INFORMATION: Synthetic

<400> SEQUENCE: 35

Cys Glu Ser Ser Lys Glu Ala Leu Ala Glu Asn Asn Leu Asn Leu Pro
1               5                   10                  15

Lys

<210> SEQ ID NO 36
<211> LENGTH: 11
<212> TYPE: PRT
<213> ORGANISM: Artificial Sequence
<220> FEATURE:
<223> OTHER INFORMATION: Monkey IL-6 portion
<220> FEATURE:
<221> NAME/KEY: misc_feature
<223> OTHER INFORMATION: Synthetic

<400> SEQUENCE: 36

Cys Phe Gln Ser Gly Phe Asn Glu Asp Thr Cys
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Monkey IL-6 portion
<220> FEATURE:
<221> NAME/KEY: misc_feature
<223> OTHER INFORMATION: Synthetic

<400> SEQUENCE: 37

Tyr Leu Gln Asn Arg Phe Glu Ser Ser Glu Glu Gln Ala Arg
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Monkey IL-6 portion
<220> FEATURE:
<221> NAME/KEY: misc_feature
<223> OTHER INFORMATION: Synthetic

<400> SEQUENCE: 38

Lys Leu Gln Ala Gln Asn Gln Trp Leu Gln Asp Met
1               5                   10

<210> SEQ ID NO 39
<211> LENGTH: 15
<212> TYPE: PRT
```

```
<213> ORGANISM: Artificial Sequence
<220> FEATURE:
<223> OTHER INFORMATION: Horse IL-6 portion
<220> FEATURE:
<221> NAME/KEY: misc_feature
<223> OTHER INFORMATION: Synthetic

<400> SEQUENCE: 39

Lys Ile Ser Ala Leu Lys Asn Glu Met Cys Asn Asn Phe Ser Lys
1               5                   10                  15

<210> SEQ ID NO 40
<211> LENGTH: 17
<212> TYPE: PRT
<213> ORGANISM: Artificial Sequence
<220> FEATURE:
<223> OTHER INFORMATION: Horse IL-6 portion
<220> FEATURE:
<221> NAME/KEY: misc_feature
<223> OTHER INFORMATION: Synthetic

<400> SEQUENCE: 40

Cys Glu Asn Ser Lys Glu Val Leu Ala Glu Asn Asn Leu Asn Leu Pro
1               5                   10                  15

Lys

<210> SEQ ID NO 41
<211> LENGTH: 11
<212> TYPE: PRT
<213> ORGANISM: Artificial Sequence
<220> FEATURE:
<223> OTHER INFORMATION: Horse IL-6 portion
<220> FEATURE:
<221> NAME/KEY: misc_feature
<223> OTHER INFORMATION: Synthetic

<400> SEQUENCE: 41

Cys Phe Gln Ser Gly Phe Asn Gln Glu Thr Cys
1               5                   10

<210> SEQ ID NO 42
<211> LENGTH: 15
<212> TYPE: PRT
<213> ORGANISM: Artificial Sequence
<220> FEATURE:
<223> OTHER INFORMATION: Horse IL-6 portion
<220> FEATURE:
<221> NAME/KEY: misc_feature
<223> OTHER INFORMATION: Synthetic

<400> SEQUENCE: 42

Glu Tyr Leu Gln Asn Glu Phe Lys Gly Glu Lys Glu Asn Ile Lys
1               5                   10                  15

<210> SEQ ID NO 43
<211> LENGTH: 13
<212> TYPE: PRT
<213> ORGANISM: Artificial Sequence
<220> FEATURE:
<223> OTHER INFORMATION: Horse IL-6 portion
<220> FEATURE:
<221> NAME/KEY: misc_feature
<223> OTHER INFORMATION: Synthetic

<400> SEQUENCE: 43

Ala Lys Leu His Ser Gln Asn Glu Trp Leu Lys Asn Thr
1               5                   10
```

-continued

```
<210> SEQ ID NO 44
<211> LENGTH: 15
<212> TYPE: PRT
<213> ORGANISM: Artificial Sequence
<220> FEATURE:
<223> OTHER INFORMATION: Dog IL-6 portion
<220> FEATURE:
<221> NAME/KEY: misc_feature
<223> OTHER INFORMATION: Synthetic

<400> SEQUENCE: 44

Lys Ile Ser Ala Leu Arg Lys Glu Met Cys Asp Lys Phe Asn Lys
1               5                   10                  15

<210> SEQ ID NO 45
<211> LENGTH: 17
<212> TYPE: PRT
<213> ORGANISM: Artificial Sequence
<220> FEATURE:
<223> OTHER INFORMATION: Dog IL-6 portion
<220> FEATURE:
<221> NAME/KEY: misc_feature
<223> OTHER INFORMATION: Synthetic

<400> SEQUENCE: 45

Cys Glu Asp Ser Lys Glu Ala Leu Ala Glu Asn Asn Leu His Leu Pro
1               5                   10                  15

Lys

<210> SEQ ID NO 46
<211> LENGTH: 11
<212> TYPE: PRT
<213> ORGANISM: Artificial Sequence
<220> FEATURE:
<223> OTHER INFORMATION: Dog IL-6 portion
<220> FEATURE:
<221> NAME/KEY: misc_feature
<223> OTHER INFORMATION: Synthetic

<400> SEQUENCE: 46

Cys Phe Gln Ser Gly Phe Asn Gln Glu Thr Cys
1               5                   10

<210> SEQ ID NO 47
<211> LENGTH: 15
<212> TYPE: PRT
<213> ORGANISM: Artificial Sequence
<220> FEATURE:
<223> OTHER INFORMATION: Dog IL-6 portion
<220> FEATURE:
<221> NAME/KEY: misc_feature
<223> OTHER INFORMATION: Synthetic

<400> SEQUENCE: 47

Asn Ile Leu Gln Asn Asn Tyr Glu Gly Asp Lys Glu Asn Val Lys
1               5                   10                  15

<210> SEQ ID NO 48
<211> LENGTH: 13
<212> TYPE: PRT
<213> ORGANISM: Artificial Sequence
<220> FEATURE:
<223> OTHER INFORMATION: Dog IL-6 portion
<220> FEATURE:
<221> NAME/KEY: misc_feature
<223> OTHER INFORMATION: Synthetic

<400> SEQUENCE: 48

Ala Ile Leu Gln Ser Gln Asp Glu Cys Val Lys His Thr
```

```
<210> SEQ ID NO 49
<211> LENGTH: 15
<212> TYPE: PRT
<213> ORGANISM: Artificial Sequence
<220> FEATURE:
<223> OTHER INFORMATION: Cat IL-6 portion
<220> FEATURE:
<221> NAME/KEY: misc_feature
<223> OTHER INFORMATION: Synthetic

<400> SEQUENCE: 49

Lys Ile Ser Ala Leu Lys Lys Glu Met Cys Asp Asn Tyr Asn Lys
1               5                   10                  15

<210> SEQ ID NO 50
<211> LENGTH: 17
<212> TYPE: PRT
<213> ORGANISM: Artificial Sequence
<220> FEATURE:
<223> OTHER INFORMATION: Cat IL-6 portion
<220> FEATURE:
<221> NAME/KEY: misc_feature
<223> OTHER INFORMATION: Synthetic

<400> SEQUENCE: 50

Cys Glu Asp Ser Lys Glu Ala Leu Ala Glu Asn Asn Leu Asn Leu Pro
1               5                   10                  15

Lys

<210> SEQ ID NO 51
<211> LENGTH: 11
<212> TYPE: PRT
<213> ORGANISM: Artificial Sequence
<220> FEATURE:
<223> OTHER INFORMATION: Cat IL-6 portion
<220> FEATURE:
<221> NAME/KEY: misc_feature
<223> OTHER INFORMATION: Synthetic

<400> SEQUENCE: 51

Cys Phe Gln Ser Gly Phe Asn Gln Glu Thr Cys
1               5                   10

<210> SEQ ID NO 52
<211> LENGTH: 15
<212> TYPE: PRT
<213> ORGANISM: Artificial Sequence
<220> FEATURE:
<223> OTHER INFORMATION: Cat IL-6 portion
<220> FEATURE:
<221> NAME/KEY: misc_feature
<223> OTHER INFORMATION: Synthetic

<400> SEQUENCE: 52

Lys Phe Leu Gln Asp Lys Tyr Glu Gly Asp Glu Glu Asn Ala Lys
1               5                   10                  15

<210> SEQ ID NO 53
<211> LENGTH: 13
<212> TYPE: PRT
<213> ORGANISM: Artificial Sequence
<220> FEATURE:
<223> OTHER INFORMATION: Cat IL-6 portion
<220> FEATURE:
<221> NAME/KEY: misc_feature
<223> OTHER INFORMATION: Synthetic
```

<400> SEQUENCE: 53

Ala Lys Leu Gln Ser Gln Glu Glu Trp Leu Arg His Thr
1               5                   10

<210> SEQ ID NO 54
<211> LENGTH: 212
<212> TYPE: PRT
<213> ORGANISM: Homo sapiens

<400> SEQUENCE: 54

Met Asn Ser Phe Ser Thr Ser Ala Phe Gly Pro Val Ala Phe Ser Leu
1               5                   10                  15

Gly Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 55
<211> LENGTH: 211
<212> TYPE: PRT
<213> ORGANISM: Mus musculus

<400> SEQUENCE: 55

Met Lys Phe Leu Ser Ala Arg Asp Phe His Pro Val Ala Phe Leu Gly
1               5                   10                  15

Leu Met Leu Val Thr Thr Thr Ala Phe Pro Thr Ser Gln Val Arg Arg
            20                  25                  30

Gly Asp Phe Thr Glu Asp Thr Thr Pro Asn Arg Pro Val Tyr Thr Thr
        35                  40                  45

Ser Gln Val Gly Gly Leu Ile Thr His Val Leu Trp Glu Ile Val Glu
    50                  55                  60

Met Arg Lys Glu Leu Cys Asn Gly Asn Ser Asp Cys Met Asn Asn Asp
65                  70                  75                  80

Asp Ala Leu Ala Glu Asn Asn Leu Lys Leu Pro Glu Ile Gln Arg Asn

```
                    85                  90                  95

Asp Gly Cys Tyr Gln Thr Gly Tyr Asn Gln Glu Ile Cys Leu Leu Lys
            100                 105                 110

Ile Ser Ser Gly Leu Leu Glu Tyr His Ser Tyr Leu Glu Tyr Met Lys
            115                 120                 125

Asn Asn Leu Lys Asp Asn Lys Lys Asp Lys Ala Arg Val Leu Gln Arg
        130                 135                 140

Asp Thr Glu Thr Leu Ile His Ile Phe Asn Gln Glu Val Lys Asp Leu
145                 150                 155                 160

His Lys Ile Val Leu Pro Thr Pro Ile Ser Asn Ala Leu Leu Thr Asp
                165                 170                 175

Lys Leu Glu Ser Gln Lys Glu Trp Leu Arg Thr Lys Thr Ile Gln Phe
            180                 185                 190

Ile Leu Lys Ser Leu Glu Glu Phe Leu Lys Val Thr Leu Arg Ser Thr
            195                 200                 205

Arg Gln Thr
    210

<210> SEQ ID NO 56
<211> LENGTH: 15
<212> TYPE: PRT
<213> ORGANISM: Artificial Sequence
<220> FEATURE:
<223> OTHER INFORMATION: Human IL-6 portion variant
<220> FEATURE:
<221> NAME/KEY: misc_feature
<223> OTHER INFORMATION: Synthetic

<400> SEQUENCE: 56

Asp Phe Leu Gln Asn Arg Phe Asp Ser Ser Asp Glu Asn Ala Arg
1               5                   10                  15

<210> SEQ ID NO 57
<211> LENGTH: 18
<212> TYPE: PRT
<213> ORGANISM: Artificial Sequence
<220> FEATURE:
<223> OTHER INFORMATION: Modified human IL-6 portion variant
<220> FEATURE:
<221> NAME/KEY: misc_feature
<223> OTHER INFORMATION: Synthetic

<400> SEQUENCE: 57

Tyr Cys Asp Phe Leu Gln Asn Arg Phe Asp Ser Ser Asp Glu Asn Ala
1               5                   10                  15

Arg Cys

<210> SEQ ID NO 58
<211> LENGTH: 212
<212> TYPE: PRT
<213> ORGANISM: Macaca mulatta

<400> SEQUENCE: 58

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Leu Pro
            20                  25                  30

Gly Glu Asp Ser Lys Asn Val Ala Ala Pro His Ser Gln Pro Leu Thr
        35                  40                  45

Ser Ser Glu Arg Ile Asp Lys His Ile Arg Tyr Ile Leu Asp Gly Ile
    50                  55                  60
```

Ser Ala Leu Arg Lys Glu Thr Cys Asn Arg Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Asp Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Glu Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Asn Leu Arg Ala
        195                 200                 205

Leu Arg Gln Met
    210

<210> SEQ ID NO 59
<211> LENGTH: 208
<212> TYPE: PRT
<213> ORGANISM: Equus caballus

<400> SEQUENCE: 59

Met Asn Ser Leu Ser Thr Ser Val Thr Pro Val Ala Phe Ser Leu
1               5                   10                  15

Gly Leu Leu Leu Val Met Ala Thr Ala Phe Pro Thr Pro Leu Pro Leu
                20                  25                  30

Gly Glu Asp Glu Thr Thr Ser Asn Gly Pro Leu Leu Thr Thr Ala Asp
            35                  40                  45

Lys Thr Lys Gln His Ile Lys Tyr Ile Leu Gly Lys Ile Ser Ala Leu
50                  55                  60

Lys Asn Glu Met Cys Asn Asn Phe Ser Lys Cys Glu Asn Ser Lys Glu
65                  70                  75                  80

Val Leu Ala Glu Asn Asn Leu Asn Leu Pro Lys Met Ala Glu Lys Asp
                85                  90                  95

Gly Cys Phe Gln Ser Gly Phe Asn Gln Glu Thr Cys Leu Met Lys Ile
            100                 105                 110

Thr Thr Gly Leu Ser Glu Phe Gln Ile Tyr Leu Glu Tyr Leu Gln Asn
        115                 120                 125

Glu Phe Lys Gly Glu Lys Glu Asn Ile Lys Thr Met Gln Ile Ser Thr
    130                 135                 140

Lys Val Leu Val Gln Ile Leu Met Gln Lys Met Lys Asn Pro Glu Val
145                 150                 155                 160

Thr Thr Pro Asp Pro Thr Ala Lys Ser Ser Leu Leu Ala Lys Leu His
                165                 170                 175

Ser Gln Asn Glu Trp Leu Lys Asn Thr Thr His Leu Ile Leu Arg
            180                 185                 190

Ser Leu Glu Asp Phe Leu Gln Phe Ser Leu Arg Ala Val Arg Ile Met
        195                 200                 205

<210> SEQ ID NO 60
<211> LENGTH: 207
<212> TYPE: PRT
<213> ORGANISM: Canis familiaris

<400> SEQUENCE: 60

Met Asn Ser Leu Ser Thr Ser Ala Phe Ser Leu Gly Leu Leu Leu Val
1               5                   10                  15

Met Ala Thr Ala Phe Pro Thr Pro Gly Pro Leu Ala Gly Asp Ser Lys
            20                  25                  30

Asp Asp Ala Thr Ser Asn Ser Leu Pro Leu Thr Ser Ala Asn Lys Val
        35                  40                  45

Glu Glu Leu Ile Lys Tyr Ile Leu Gly Lys Ile Ser Ala Leu Arg Lys
    50                  55                  60

Glu Met Cys Asp Lys Phe Asn Lys Cys Glu Asp Ser Lys Glu Ala Leu
65                  70                  75                  80

Ala Glu Asn Asn Leu His Leu Pro Lys Leu Glu Gly Lys Asp Gly Cys
                85                  90                  95

Phe Gln Ser Gly Phe Asn Gln Glu Thr Cys Leu Thr Arg Ile Thr Thr
            100                 105                 110

Gly Leu Val Glu Phe Gln Leu His Leu Asn Ile Leu Gln Asn Asn Tyr
        115                 120                 125

Glu Gly Asp Lys Glu Asn Val Lys Ser Val His Met Ser Thr Lys Ile
    130                 135                 140

Leu Val Gln Met Leu Lys Ser Lys Val Lys Asn Gln Asp Glu Val Thr
145                 150                 155                 160

Thr Pro Asp Pro Thr Thr Asp Ala Ser Leu Gln Ala Ile Leu Gln Ser
                165                 170                 175

Gln Asp Glu Cys Val Lys His Thr Thr Ile His Leu Ile Leu Arg Ser
            180                 185                 190

Leu Glu Asp Phe Leu Gln Phe Ser Leu Arg Ala Val Arg Ile Met
        195                 200                 205

<210> SEQ ID NO 61
<211> LENGTH: 208
<212> TYPE: PRT
<213> ORGANISM: Felis catus

<400> SEQUENCE: 61

Met Thr Phe Leu Ser Thr Ser Ala Phe Ser Pro Leu Ala Phe Ser Leu
1               5                   10                  15

Gly Leu Leu Leu Val Val Ala Thr Ala Phe Pro Thr Pro Gly Pro Leu
            20                  25                  30

Gly Gly Asp Ala Thr Ser Asn Arg Leu Pro Leu Thr Ser Ala Asp Lys
        35                  40                  45

Met Glu Glu Leu Ile Lys Tyr Ile Leu Gly Lys Ile Ser Ala Leu Lys
    50                  55                  60

Lys Glu Met Cys Asp Asn Tyr Asn Lys Cys Glu Asp Ser Lys Glu Ala
65                  70                  75                  80

Leu Ala Glu Asn Asn Leu Asn Leu Pro Lys Leu Ala Glu Lys Asp Gly
                85                  90                  95

Cys Phe Gln Ser Gly Phe Asn Gln Glu Thr Cys Leu Thr Arg Ile Thr
            100                 105                 110

Thr Gly Leu Gln Glu Phe Gln Ile Tyr Leu Lys Phe Leu Gln Asp Lys
        115                 120                 125

Tyr Glu Gly Asp Glu Glu Asn Ala Lys Ser Val Tyr Thr Ser Thr Asn

-continued

```
            130                 135                 140
Val Leu Leu Gln Met Leu Lys Arg Lys Gly Lys Asn Gln Asp Glu Val
145                 150                 155                 160

Thr Ile Pro Val Pro Thr Val Glu Val Gly Leu Gln Ala Lys Leu Gln
                165                 170                 175

Ser Gln Glu Glu Trp Leu Arg His Thr Thr Ile His Leu Thr Leu Arg
            180                 185                 190

Arg Leu Glu Asp Phe Leu Gln Phe Ser Leu Arg Ala Val Arg Ile Met
            195                 200                 205
```

ANTI-IL-6 VACCINE COMPOSITION

FIELD OF THE INVENTION

The present invention relates to an anti-IL-6 vaccine composition, as well as to the antibodies obtainable using this composition.

TECHNICAL BACKGROUND

Interleukin-6 (IL-6) is secreted by numerous blood cells. It is a 26-kDa protein composed of 183 amino acids in humans (Swissprot reference P05231). It can exert its biological effects on numerous cell types via specific membrane and soluble receptors.

IL-6 is one of the three major inflammatory cytokines, with IL-1 and TNF (Woo (1993) Clin. Exp. Rheumatol. 11 Suppl. 9:S29-32), inducing in particular the production of acute phase proteins by the liver (Nijsten et al. (1986) Lancet 2:921.16). IL-6 also plays an important role in bone and cartilage degradation (Jilka et al. (1992) Science 257:88-91, 1992), as well as in cartilage quality and proliferation of the synovial fibroblasts. In humans, it has been shown that overproduction of IL-6 is associated with rheumatoid arthritis (Robak et al. (1998) Mediators Inflamm. 7: 347-53) and it has been shown in several murine models of collagen-induced arthritis that IL-6 was necessary to the development of the disease, the mice in which the expression of IL-6 was abolished being completely protected (Alonzi et al. (1998) J. Exp. Med 187:461-8).

In the same way, the role of IL-6 as a primer has been demonstrated in other arthritic diseases, such as juvenile idiopathic arthritis, and also in chronic inflammatory diseases of the intestine (MICI) in humans (Mitsuyama et al. (1995) Gut 36:45-49), as well as in disseminated lupus erythematosus, in which an increase in IL-6 in the serum and an abnormal expression of the IL-6Rα receptor have been noted in a murine model. Moreover, the addition of exogenous IL-6 leads to increased production of auto-antibodies and more rapid progression of glomerulonephritis (Ryffel et al. (1994) Am. J. Pathol. 144:927-37).

Generally, pro-inflammatory cytokines such as IL-6, TNF, and IL-1 can be involved in the development of all of the chronic inflammatory diseases, such as chronic inflammatory diseases of the intestine, such as Crohn's disease and haemorrhagic rectocolitis or ulcerous colitis, arthritic diseases, in particular rheumatoid arthritis, juvenile rheumatoid arthritis, psoriatic arthritis, arthrosis, refractory rheumatoid arthritis, chronic non-rheumatoid arthritis, or ankylosing spondylitis, chronic or IL-6-related inflammatory bone diseases, in particular a bone resorption disorder or osteoporosis, chronic or IL-6-related inflammatory diseases associated with an infection, such as septic shock, endotoxin shock, septicaemia, HCV hepatitis, malaria, meningitis, AIDS or HIV infections, chronic or IL-6-related inflammatory diseases of the cardiovascular system, such as atherosclerosis, ischaemia-reperfusion lesions, coronary diseases, and vasculitis, such as Behçet's disease or Wegener's granulomatosis, auto-immune diseases, such as scleroderma, in particular systemic scleroderma, lupus erythematosus, in particular disseminated lupus erythematosus, multiple sclerosis, or psoriasis, diseases linked to a graft, such as graft-versus-host reactions and graft rejections and traumas, allergies, in particular allergic asthma and skin disorders due to delayed hypersensitivity reactions, immune deficiencies, such as common variable immunodeficiency (CVID), chronic or IL-6-related inflammatory diseases of the respiratory system, in particular respiratory distress syndrome or pulmonary fibrosis, cancers having a chronic or IL-6-related inflammatory component, such as plasmacytoma, colorectal cancer, recurrent ovarian cancer, lymphoproliferative syndrome, multiple myeloma, in particular refractory multiple myeloma, or myeloproliferative syndrome, diabetes, in particular juvenile diabetes, amyloidosis, in particular Alzheimer's disease, uveitis, in particular in its chronic recurrent form, cachexia, or endometriosis.

Several strategies have been envisaged in an attempt to limit the harmful effects of IL-6.

Thus, a humanized monoclonal antibody, Tocilizumab, directed against the IL-6Rα receptor, is clinically effective in the treatment of rheumatoid arthritis in adults (Patel & Moreland (2010) Drug Design, Development and Therapy 4:263-278).

Moreover, monoclonal antibodies directly targeting the IL-6 cytokine are currently being developed in the context of the treatment of auto-immune diseases, such as the antibodies CNTO328 (US 2008/0081041) and CNTO136 (US 2010/0138945), but for the time being it does not seem that their clinical effectiveness has been established.

However, approaches making use of monoclonal antibodies, if they can be proved effective, are often expensive to implement, in particular because they require regular administrations of these antibodies.

In fact, a vaccination method for combating IL-6-related immune disorders using a human IL-6 mutein, Santl (De Benedetti et al. (2001) J. Immunol. 166:4334-4340; U.S. Pat. No. 6,706,261) has been described, but this work does not seem to have resulted in clinical development. Moreover, the vaccination of mice using mouse IL-6 mutants (mIL-6) makes it possible to obtain a protective immune response vis-à-vis collagen-induced arthritis or experimental allergic encephalitis (Galle et al. (2007) Int. Immunopharmacol. 7:1704-1713). However, in this case also, this work does not seem to have resulted in clinical development.

DESCRIPTION OF THE INVENTION

The present invention results from the unexpected demonstration, by the inventors, that peptides derived from certain parts of IL-6 made it possible to generate a protective immune response vis-à-vis IL-6.

The present invention therefore relates to a pharmaceutical composition, in particular a vaccine composition, comprising, by way of active ingredient:

at least one polypeptide comprising, or consisting of:
a first sequence consisting of (i) a first portion of at least 8 contiguous amino acids selected from within the sequence extending from amino acids 58 to 78 of IL-6 and of at the most 30 contiguous amino acids selected from within the complete IL-6 sequence, or (ii) a variant sequence exhibiting at least 75% identity with the first portion; and/or a second sequence consisting of (i) a second portion of at least 8 contiguous amino acids selected from within the sequence extending from amino acids 73 to 94 of IL-6 and of at the most 30 contiguous amino acids selected from within the complete IL-6 sequence, or (ii) a variant sequence exhibiting at least 75% identity with the second portion; and/or a third sequence consisting of (i) a third portion of at least 8 contiguous amino acids selected from within the sequence extending from amino acids 96 to 111 of IL-6 and of at the most 30 contiguous amino acids selected from within the complete IL-6 sequence, or (ii) a variant sequence exhibiting at least 75% identity with the third portion; and/or a fourth sequence consisting (i) of a fourth portion of at least 8 contiguous amino acids selected from within the sequence extending from amino acids 122 to 141 of IL-6 and of at the most 30 contiguous amino acids selected from within the complete IL-6 sequence, or (ii) a variant sequence exhibiting at least 75% identity with the fourth portion; and/or a fifth sequence consisting (i) of a fifth portion of at least 8 contiguous amino acids selected from within the sequence extending from amino acids 172 to 189 of IL-6 and of at the most 30 contiguous amino acids selected from within the complete IL-6 sequence, or (ii) by a variant sequence exhibiting at least 75% identity with the fifth portion; or at least one polynucleotide encoding the above polypeptide, optionally in combination with at least one pharmaceutically acceptable vehicle, provided that a polypeptide constituted by the variant sequences makes it possible to elicit an immune response directed against IL-6 and provided that the polypeptide is different from IL-6 and that it is not constituted by a portion of more than 30 contiguous amino acids of IL-6.

In a particular embodiment, the present invention also relates to the pharmaceutical composition as defined above for use in the prevention or treatment of IL-6-related diseases or chronic inflammatory diseases.

The present invention also relates to a polypeptide as defined above, as well as a polynucleotide encoding a polypeptide as defined above.

In a particular embodiment, the invention also relates to the polypeptide as defined above, and the nucleic acid as defined above, for use as a medicament, in particular in the prevention or treatment of IL-6-related diseases or chronic inflammatory diseases.

Moreover, the present invention also relates to a method for the prevention or treatment of IL-6-related diseases or chronic inflammatory diseases in an individual, in which a prophylactically or therapeutically effective quantity of a pharmaceutical composition as defined above, of a polypeptide as defined above, or of a polynucleotide as defined above is administered to the individual.

Interleukin 6 (IL-6), also sometimes called B-cell stimulatory factor 2 (BSF-2), CTL differentiation factor (CDF), hybridoma growth factor, or interferon β-2 (IFN-β-2) is well known to a person skilled in the art. Numerous IL-6 sequences originating from various animal species are available in sequence databases. By way of example, a mouse IL-6 (mIL-6) is described in the UniProt/Swissprot database under the reference P08505 (SEQ ID NO: 55) and a human IL-6 is described in the UniProt/Swissprot database under the reference P05231 (SEQ ID NO: 54). As understood here, the numbering of the IL-6 amino acids starts on the first amino acid forming the N-terminal end of the complete IL-6 encoded by the open reading frame of the IL-6 gene, i.e. including its peptide signal.

The polypeptide according to the invention is preferably an immunogen, i.e. a polypeptide which elicits an immune reaction, in particular an anti-IL-6 immune reaction, upon its administration to an individual.

As will be clear to one of skill in the art, where the first portion, the second portion, the third portion, the fourth portion and the fifth portion are said to consist of at the most 30 contiguous amino acids selected from within the complete IL-6 sequence, these portions still always respectively comprise at least 8 contiguous amino acids respectively selected from within the sequence extending from amino acids 58 to 78, 73 to 94, 96 to 111, 122 to 141, and 172 to 189 of IL-6.

Besides, as will also be clear to one of skill in the art, the expression "consist of" and "constituted by" are considered equivalent. The expression "comprise" has a broader meaning and is considered equivalent to "include" or "contain".

Preferably, the first portion, the second portion, the third portion, the fourth portion and the fifth portion according to the invention consist of at least 9, 10, 11, 12 contiguous amino acids respectively selected from within the sequence extending from amino acids 58 to 78, 73 to 94, 96 to 111, 122 to 141, and 172 to 189 of IL-6 or respectively consist of at least the sequence extending from amino acids 58 to 78, 73 to 94, 96 to 111, 122 to 141, and 172 to 189 of IL-6.

Preferably also, the first portion, the second portion, the third portion, the fourth portion and the fifth portion according to the invention respectively consist of at the most 29, 28, 27, 26, 25, 24, 23, 22, 21, 20 contiguous amino acids selected from within the complete IL-6 sequence, or respectively consist at the most of amino acids 58 to 78, 73 to 94, 96 to 111, 122 to 141, and 172 to 189 of IL-6.

Preferably, the IL-6 according to the invention is selected from the group consisting of human IL-6, mouse IL-6, monkey, in particular macaque, IL-6, horse IL-6, dog IL-6 and cat IL-6, and particularly preferably the IL-6 according to the invention is human IL-6.

By way of example, macaque IL-6 is represented by the SwissProt database reference P51494 (SEQ ID NO: 58), horse IL-6 is represented by the SwissProt database reference Q95181 (SEQ ID NO: 59), dog IL-6 is represented by the SwissProt database reference P41323 (SEQ ID NO: 60) and cat IL-6 is represented by the SwissProt database reference P41683 (SEQ ID NO: 61).

Preferably, when the IL-6 according to the invention is human IL-6 then, preferably, the first portion, the second portion, the third portion, the fourth portion and the fifth portion according to the invention consist of at least 8, 9, 10, 11, 12 contiguous amino acids respectively selected from within the sequence extending from amino acids 63 to 78, 78 to 94, 101 to 111, 127 to 141 and 177 to 198 of human IL-6 or respectively consist at least of the sequence extending from amino acids 63 to 78, 78 to 94, 101 to 111, 127 to 141 and 177 to 198 of human IL-6.

Similarly, also preferably, the first portion, the second portion, the third portion, the fourth portion and the fifth portion according to the invention respectively consist of at the most 29, 28, 27, 26, 25, 24, 23, 22, 21, 20 contiguous amino acids selected from within the complete human IL-6 sequence, or respectively consist at the most of amino acids 63 to 78, 78 to 94, 101 to 111, 127 to 141 and 177 to 198 of human IL-6.

A variant sequence according to the invention, which exhibits at least 75% identity with one of the first, second, third, fourth, and fifth portions above, preferably exhibits at least 80%, 85%, 90%, 95% or 98% identity with one of the first, second, third, fourth, and fifth portions above. Preferably also, a variant sequence according to the invention has the same number of amino acids than the portion it derives from. More preferably, a variant sequence according to the invention comprises at the most 29, 28, 27, 26, 25, 24, 23, 22, 21, 20 amino acids.

As understood here, the percentage identity between two peptide sequences can be determined by carrying out an optimum alignment over the whole length of the sequences, by determining the number of aligned positions for which the amino acids are identical in each sequence and by dividing this number by the total number of amino acids in the longer of the two sequences. The optimum alignment is that which gives the highest percentage identity between the two sequences.

Preferably, the first, the second, the third, the fourth and the fifth portions according to the invention respectively consist of SEQ ID NO: 1, SEQ ID NO: 2, SEQ ID NO: 3, SEQ ID NO: 4 and SEQ ID NO: 5.

SEQ ID NO: 1 to 5 respectively represent the portions 63 to 78, 78 to 94, 101 to 111, 127 to 141 and 177 to 198 respectively of the human IL-6 represented by SEQ ID NO: 54.

| | |
|---|---|
| GISALRKETCNKSNMC | SEQ ID NO: 1 |
| CESSKEALAENNLNLPK | SEQ ID NO: 2 |
| CFQSGFNEETC | SEQ ID NO: 3 |
| EYLQNRFESSEEQAR | SEQ ID NO: 4 |
| TKLQAQNQWLQDM | SEQ ID NO: 5 |

Thus, also preferably, a variant sequence according to the invention exhibits at least 75%, 80%, 85%, 90%, 95% or 98% identity with SEQ ID NO: 1, SEQ ID NO: 2, SEQ ID NO: 3, SEQ ID NO: 4, SEQ ID NO: 4 or SEQ ID NO: 5.

By way of example, a variant sequence according to the invention is selected from the group constituted by:
SEQ ID NO: 8 for the first sequence,
SEQ ID NO: 9 for the second sequence,
SEQ ID NO: 10 for the third sequence,
SEQ ID NO: 6, SEQ ID NO: 11, SEQ ID NO: 56 for the fourth sequence, and
SEQ ID NO: 7, SEQ ID NO: 12 for the fifth sequence.
SEQ ID NO: 8 is a variant sequence of SEQ ID NO: 1; SEQ ID NO: 9 is a variant sequence of SEQ ID NO: 2; SEQ ID NO: 10 is a variant sequence of SEQ ID NO: 3; SEQ ID NO: 6, 11 and 56 are variant sequences of SEQ ID NO: 4; and SEQ ID NO: 7 and 12 are variant sequences of SEQ ID NO: 5.

| | |
|---|---|
| GISALRKETCNKSNMC | SEQ ID NO: 1 |
| GISAVRKDTCNKSQMC | SEQ ID NO: 8 |
| CESSKEALAENNLNLPK | SEQ ID NO: 2 |
| CESSKDAIAENQLNLPK | SEQ ID NO: 9 |
| CFQSGFNEETC | SEQ ID NO: 3 |
| CFNSGFNEDTC | SEQ ID NO: 10 |
| EYLQNRFESSEEQAR | SEQ ID NO: 4 |
| EFLQNRFESSEEQAR | SEQ ID NO: 6 |
| EFLQNRFDSSDENAR | SEQ ID NO: 11 |
| DFLQNRFDSSDENAR | SEQ ID NO: 56 |
| TKLQAQNQWLQDM | SEQ ID NO: 5 |
| TKCQAQNQWLQDM | SEQ ID NO: 7 |
| TKCQANQQWLQEM | SEQ ID NO: 12 |

Particularly preferably, the first sequence according to the invention is constituted by a sequence selected from the group constituted by SEQ ID NO: 1, SEQ ID NO: 8, SEQ ID NO: 24, SEQ ID NO: 34, SEQ ID NO: 39, SEQ ID NO: 44 and SEQ ID NO: 49.

Particularly preferably, the second sequence according to the invention is constituted by a sequence selected from the group constituted by SEQ ID NO: 2, SEQ ID NO: 9, SEQ ID NO: 25, SEQ ID NO: 35, SEQ ID NO: 40, SEQ ID NO: 45 and SEQ ID NO: 50.

Particularly preferably, the third sequence according to the invention is constituted by a sequence selected from the group constituted by SEQ ID NO: 3, SEQ ID NO: 10, SEQ ID NO: 26, SEQ ID NO: 36, SEQ ID NO: 41, SEQ ID NO: 46, and SEQ ID NO: 51.

Particularly preferably, the fourth sequence according to the invention is constituted by a sequence selected from the group constituted by SEQ ID NO: 4, SEQ ID NO: 6, SEQ ID NO: 11, SEQ ID NO: 56, SEQ ID NO: 27, SEQ ID NO: 37, SEQ ID NO: 42, SEQ ID NO: 47 and SEQ ID NO: 52.

Particularly preferably, the fifth sequence according to the invention is constituted by a sequence selected from the group constituted by SEQ ID NO: 5, SEQ ID NO: 7, SEQ ID NO: 12, SEQ ID NO: 28, SEQ ID NO: 25, SEQ ID NO: 38, SEQ ID NO: 43, SEQ ID NO: 48 and SEQ ID NO: 53.

SEQ ID NO: 24 to 28 represent portions or variant sequences of mouse IL-6.

SEQ ID NO: 34 to 38 represent portions of monkey, in particular macaque, IL-6.

SEQ ID NO: 39 to 43 represent portions of horse IL-6.

SEQ ID NO: 44 to 48 represent portions of dog IL-6.

SEQ ID NO: 49 to 53 represent portions of cat IL-6.

Particularly preferably, the first sequence, the second sequence, the third sequence, the fourth sequence and the fifth sequence according to the invention respectively consist of SEQ ID NO: 1, SEQ ID NO: 2, SEQ ID NO: 3, SEQ ID NO: 6 and SEQ ID NO: 7.

The variant sequence according to the invention is such that a polypeptide consisting of the variant sequence must make it possible to elicit an immune response directed against IL-6; i.e. the administration of such a peptide, optionally cyclized by the formation of at least one intercysteine disulfide bond, if necessary after the addition of one or two cysteines within the peptide, and/or at its the N-terminal end and/or at its C-terminal end, the peptide being optionally coupled to a carrier molecule, in particular a carrier protein, such as KLH (Keyhole Limpet Hemocyanin), in an animal, such as a mouse, a rat or a rabbit, causes the production of antibodies directed against an IL-6, in particular an IL-6 of the same species as that to which the sequence with which the variant sequence exhibits the highest percentage of identity belongs. A person skilled in the art knows well how to determine whether an antibody is directed against IL-6, in particular by carrying out an ELISA test. Preferably, the antibodies elicited by administration of the peptide are blocking, i.e. they prevent IL-6 from exerting all or part, in particular at least 10%, 25%, 50%, 75%, of its activity, for example measured in vitro as indicated in Example 5 below.

The polypeptide according to the invention preferably comprises at the most 200, 150, 100, 90, 80, 70, 60, 50, 40, 30, 25, 24, 23, 22, 21 or 20 amino acids. It is different from IL-6 and is not constituted by a portion of more than 30, 25, 24, 23, 22, 21 or 20 contiguous IL-6 amino acids. As is well understood by a person skilled in the art this does not exclude the possibility of its being constituted by two or more portions of IL-6 of at the most 30, 25, 24, 23, 22, 21 or 20 contiguous amino acids, to the extent that these portions are not arranged so as to reconstitute an IL-6 portion of more than 30, 25, 24, 23, 22, 21 or 20 contiguous amino acids. Moreover, the polypeptide according to the invention can also comprise sequences not originating from IL-6, and in particular sequences comprising epitopes belonging to other proteins.

The polypeptide according to the invention is preferably cyclized. This cyclization can be of any type known to a person skilled in the art, however, here it is preferred that the polypeptide is cyclized by the formation of an inter-cysteine disulfide bond, i.e. between the —SH radicals of two cysteines. The cysteines can already be present in the variant sequence according to the invention or in the first, second, third, fourth, and fifth portions according to the invention, or be added within these sequences, as well as at their N-terminal and/or C-terminal end.

Thus, preferably, the polypeptide according to the invention is constituted by a sequence selected from the group constituted by SEQ ID NO: 1, SEQ ID NO: 13, SEQ ID NO: 3, SEQ ID NO: 14 and SEQ ID NO: 15, and is preferably cyclized by the formation of a disulfide bond between the —SH radicals of the cysteines.

SEQ ID NO: 13 represents a sequence SEQ ID NO: 2 to which a cysteine has been added at the C-terminal end.

SEQ ID NO: 14 represents a sequence SEQ ID NO: 6 to which a cysteine has been added at the N-terminal end and a cysteine has been added at the C-terminal end.

SEQ ID NO: 15 represents a sequence SEQ ID NO: 7 to which a cysteine has been added at the C-terminal end.

Moreover, SEQ ID NO: 7 represents a sequence SEQ ID NO: 5 in which the leucine in third position has been replaced by a cysteine.

Moreover, the polypeptide according to the invention can comprise post-translational modifications, such as glycosylations, methylations, acylations, in particular by fatty acids, or phosphorylations. In particular, the N-terminal end of the polypeptide according to the invention can be acetylated and the C-terminal end can be modified by amidation.

The polypeptide according to the invention can also comprise one or more analogues or derivatives of amino acids, including non-natural or non-standard amino acids.

Also preferably, the polypeptide according to the invention is bound, in particular by a covalent bond, to a macromolecule, in particular a carrier protein, in particular the Keyhole Limpet Hemocyanin (KLH) protein, a metalloprotein extracted from *Megathura crenulata* well known to a person skilled in the art. Other carrier proteins capable of being used according to the invention include, in particular, the hepatitis B surface antigen (HBsAg), bovine serum albumin (BSA), diphtheria toxoid (DT) and tetanus toxoid (TT). Preferably, the carrier macromolecule according to the invention is an immunological carrier macromolecule, i.e. a macromolecule eliciting or enhancing an immune reaction against the polypeptides bound to it.

The binding of the polypeptide according to the invention to a macromolecule, in particular a carrier protein, can be carried out using a coupling agent, such as bisdiazonium-benzidine (BDB) or glutaraldehyde. Other coupling agents, such as carbodiimides and m-maleimidobenzoyl-n-hydroxy-succinimide ester (MBS) can also be used. When BDB is used, it is preferably bound to a tyrosine which, if it is not present in the polypeptide according to the invention, can be added, in particular at its N-terminal or C-terminal end. Moreover, when a tyrosine is present in a portion according to the invention in an undesired position, it is possible to utilize, at that point, a variant sequence in which the tyrosine is replaced by another amino acid, such as a phenylalanine. This possibility is in particular illustrated by the sequences SEQ ID NO: 6, 11 and 56 with respect to the portion of sequence SEQ ID NO: 4.

Thus, quite particularly preferably, the polypeptide according to the invention is bound to the KLH carrier protein in order to form a construction represented by a formula selected from the group constituted by the following formulae:

$$\text{KLH-[BDB-Y-\underline{GISALRKETCNKSNMC}}_{+Amide}], \quad \text{(SEQ ID NO: 16)}$$

$$[_{Acetyl+}\text{\underline{CESSKEALAENNLNLPKC}-Y-BDB]-KLH}, \quad \text{(SEQ ID NO: 17)}$$

$$\text{KLH-[Gluta-\underline{CFQSGFNEETC}}_{+Amide}], \quad \text{(SEQ ID NO: 3)}$$

$$\text{KLH-[BDB-Y-\underline{CEFLQNRFESSEEQARC}}_{+Amide}], \quad \text{(SEQ ID NO: 18)}$$

and $$[_{Acetyl+}\text{\underline{TKCQAQNQWLQDMC}-Y-BDB]-KLH}, \quad \text{(SEQ ID NO: 19)}$$

where KLH denotes the carrier protein Keyhole Limpet Hemocyanin, BDB denotes bisdiazonium-benzidine, Gluta denotes glutaraldehyde, Acetyl+ indicates that the N-terminal end is acetylated, Amide+ indicates that the C-terminal end is modified by amidation, the brackets indicate that one or more polypeptides are bound to the carrier protein and the underlined part represents the polypeptide according to the invention.

The polypeptide according to the invention can be prepared by any method known in the state of the art and in particular by chemical synthesis. It can also be prepared by expression of the polynucleotide according to the invention. In this case, the polypeptide according to the invention can then be expressed fused to a virus-like particle (VLP) which will then act as a carrier protein, as described in the international application WO 05/117983 for TNF for example.

The polynucleotide according to the invention is RNA or DNA, preferably DNA. It is preferred that the polynucleotide according to the invention is operatively bound to a prokaryotic and/or eukaryotic promoter sequence, in particular from a mammal or virus. Moreover, the polynucleotide according to the invention can be included in a vector, such as a plasmid or a virus.

The present invention also relates to an anti-IL-6 antibody or aptamer specifically directed against a polypeptide comprising, or consisting of:
  a first sequence consisting of (i) a first portion of at least 8 contiguous amino acids selected from within the sequence extending from amino acids 58 to 78 of IL-6 and of at the most 30 contiguous amino acids selected from within the complete IL-6 sequence, or (ii) a variant sequence exhibiting at least 75% identity with the first portion; and/or a second sequence consisting of (i) a second portion of at least 8 contiguous amino acids selected from within the sequence extending from amino acids 73 to 94 of IL-6 and of at the most 30 contiguous amino acids selected from within the complete IL-6 sequence, or (ii) a variant sequence exhibiting at least 75% identity with the second portion; and/or a third sequence consisting of (i) a third portion of at least 8 contiguous amino acids selected from within the sequence extending from amino acids 96 to 111 of IL-6 and of at the most 30 contiguous amino acids selected from within the complete IL-6 sequence, or (ii) a variant sequence exhibiting at least 75% identity with the third portion; and/or a fourth sequence consisting (i) of a fourth portion of at least 8 contiguous amino acids selected from within the sequence extending from amino acids 122 to 141 of IL-6 and of at the most 30 contiguous amino acids selected from within the complete IL-6 sequence, or (ii) a variant sequence exhibiting at least 75% identity with the fourth portion; and/or a fifth sequence consisting (i) of a fifth portion of at least 8 contiguous amino acids selected from within the sequence extending from amino acids 172 to 189 of IL-6 and of at the most 30 contiguous amino acids selected from within the complete IL-6 sequence, or (ii) by a variant sequence exhibiting at least 75% identity with the fifth portion; provided that a polypeptide constituted by the variant sequences makes it possible to elicit an immune response directed against IL-6 and provided that the polypeptide comprises no more than 2 amino acids in addition to the first, second, third, fourth and fifth sequence.

The antibody and aptamer according to the invention are said to be specifically directed against a polypeptide as defined above when they essentially do not bind to another polypeptide, which does not comprises the polypeptide defined above, under conditions allowing the antibody and aptamer according to the invention to bind to the polypeptides against which they are specifically directed.

The antibody according to the invention can be polyclonal or monoclonal, preferably monoclonal. Moreover, as understood here, the word "antibody" includes whole antibodies as well as fragments of antibodies comprising at least one antigen-binding part, such as the Fab, F(ab')$_2$, and scFv fragments.

The antibodies can be from any species, in particular mouse, rat, rabbit or camelid. Moreover, they can also be humanized. The antibodies according to the invention can be obtained by immunization of an animal using a polypeptide according to the invention.

As understood here, the aptamers are nucleic acids, in particular RNA, capable of binding specifically to a target molecule, such as a protein. The aptamers can in particular be obtained by implementation of the SELEX technique well known to a person skilled in the art, from the polypeptides according to the invention.

Preferably, the first, the second, the third, the fourth and the fifth sequence, as well as the variant sequence, of the polypeptide against which the antibody, in particular the monoclonal antibody, and the aptamer according to the invention are specifically directed are as defined above for the polypeptide and the pharmaceutical composition according to the invention.

Moreover, it is preferred that the polypeptide against which the antibody, in particular the monoclonal antibody, and the aptamer according to the invention are specifically directed, is cyclized, in particular by formation of an intercysteine disulfide bond, i.e. between the —SH radicals of two cysteines. The cysteines can be already present in the variant sequence according to the invention or in the first, second, third, fourth, and fifth sequences according to the invention, or be added within its sequences, as well as at their N-terminal and/or C-terminal end.

Thus, preferably, the polypeptide against which the antibody, in particular the monoclonal antibody, and the aptamer according to the invention are specifically directed consists of a sequence selected from the group consisting of SEQ ID NO: 1, SEQ ID NO: 13, SEQ ID NO: 3, SEQ ID NO: 14 and SEQ ID NO: 15, and is preferably cyclized by the formation of a disulfide bond between the —SH radicals of the cysteines.

In a preferred embodiment, the invention also relates to an antibody or an aptamer as defined above for use as a medicament. The invention also relates to a pharmaceutical composition comprising, by way of active ingredient, at least one antibody or aptamer as defined above, optionally in combination with a pharmaceutically acceptable vehicle.

In another preferred embodiment, the invention also relates to an antibody or aptamer as defined above, or a pharmaceutical composition comprising an antibody or aptamer according to the invention as defined above, for use in the prevention or treatment of IL-6-related diseases or chronic inflammatory diseases.

The present invention also relates to a method for the prevention or treatment of IL-6-related diseases or chronic inflammatory diseases in an individual, in which a prophylactically or therapeutically effective quantity of an antibody or aptamer as defined above or a pharmaceutical composition comprising an antibody or aptamer according to the invention as defined above, is administered to the individual.

The IL-6-related diseases or the chronic inflammatory diseases according to the invention are preferably selected from the group consisting of:

chronic inflammatory diseases of the intestine, such as Crohn's disease and haemorrhagic rectocolitis or ulcerous colitis, arthritic diseases, in particular rheumatoid arthritis, juvenile rheumatoid arthritis, psoriatic arthritis, arthrosis, refractory rheumatoid arthritis, chronic non-rheumatoid arthritis, or ankylosing spondylitis, chronic or IL-6-related inflammatory bone diseases, in particular a bone resorption disorder or osteoporosis, chronic or IL-6-related inflammatory diseases associated with an infection, such as septic shock, endotoxin shock, septicaemia, HCV hepatitis, malaria, meningitis, AIDS or HIV infections, chronic or IL-6-related inflammatory diseases of the cardiovascular system, such as atherosclerosis, ischaemia-reperfusion lesions, coronary diseases, and vasculitis, such as Behçet's disease or Wegener's granulomatosis, auto-immune diseases, such as scleroderma, in particular systemic scleroderma (also known as systemic sclerosis), lupus erythematosus, in particular disseminated lupus erythematosus, multiple sclerosis, or psoriasis, diseases linked to a graft, such as graft-versus-host reactions and graft rejections and traumas, allergies, in particular allergic asthma and skin disorders due to delayed hypersensitivity reactions, immune deficiencies, such as common variable immunodeficiency (CVID), chronic or IL-6-related inflammatory diseases of the respiratory system, in particular respiratory distress syndrome or pulmonary fibrosis, cancers having a chronic or IL-6-related inflammatory component, such as plasmacytoma, colorectal cancer, recurrent ovarian cancer, lymphoproliferative syndrome, multiple myeloma, in particular refractory multiple myeloma, or myeloproliferative syndrome,
diabetes, in particular juvenile diabetes,
amyloidosis, in particular Alzheimer's disease,
uveitis, in particular in its chronic recurrent form,
cachexia, and
endometriosis.

In particular, the IL-6-related diseases or chronic inflammatory diseases are more preferably selected from the group consisting of rheumatoid arthritis, chronic inflammatory diseases of the intestine, such as Crohn's disease and haemorrhagic rectocolitis, lupus erythematosus, psoriasis, multiple myeloma, and colorectal cancer.

The individuals intended to be vaccinated or treated according to the invention are animals or humans.

When they are used in a prophylactic or therapeutic context the polypeptide and the antibody according to the invention can be combined with a pharmaceutically acceptable vehicle.

As understood here, a "pharmaceutically acceptable vehicle" includes all of the compounds, in particular the excipients, which can be administered to an individual in conjunction with a pharmacologically active ingredient.

Moreover, when it is used in a vaccine or prophylactic context the polypeptide according to the invention can be combined with an adjuvant. The adjuvant can be of any type suited to enhancing the immune response of an individual, animal or human, to the administration of a polypeptide. It can thus be complete or incomplete Freund's adjuvant, ISA51, alum or calcium phosphate for example, the ISA51 and alum being preferred. The adjuvant can be combined with the polypeptide according to the invention by producing a 1/1 mixture by volume of a solution of adjuvant and a solution comprising the polypeptide.

In the context of the invention, the polypeptide according to the invention can be administered in doses ranging for example from 1 ng to 1 g, preferably from 1 µg to 1 mg. The polypeptide is preferably administered by intravenous, intradermal, sub-cutaneous, or intramuscular route. The administration regime can, for example, consist of 1 administration every 15 days over 2 months, then 1 administration every 3 to 6 months, for as long as desired to obtain a prophylactic or therapeutic effect.

The invention is further illustrated using the following figures and non-limitative examples.

EXAMPLES

Example 1

Recognition of the Whole Murine IL-6 (mIL-6) Cytokine and Cross-Reactivity Against the Human IL-6 (hIL-6) Cytokine by Serums from Mice Immunized with Peptides Derived from mIL-6

Six peptides derived from murine IL-6 were chemically synthesized and coupled to a carrier protein, KLH (Keyhole Limpet Hemocyanin), five using the coupling agent bisdiazonium-benzidine (BDB) and one with glutaraldehyde. These peptides were then cyclized by the formation of disulfide bonds between cysteines (added or already present).

For each peptide, Oncins France 1 mice (OF1, Charles River Laboratories, L'Arbresle, France) free from specific pathogenic organisms were immunized by intra-muscular route with 100 µg of peptides derived from murine IL-6 mP1, mP2, mP3, mP4, mP5, and mP6 (see Table 1) in complete Freund's adjuvant (CFA) at the start of the experiment (D0) (n=4 per peptide).

TABLE 1

Peptides derived from mIL-6 (underlined) used for the immunization

| Peptide | IL-6 region | Sequence | SEQ ID NO |
|---|---|---|---|
| mP1 | 61-75 | BDB-Y-$E_{61}$IVEMRKELCNGNSD$_{75}$C$_{+Amide}$ | 29 |
| mP2 | 76-92 | $_{Acetyl+}$C$_{76}$MNNDDALAENNLKLPE$_{92}$C-Y-BDB | 30 |
| mP3 | 99-109 | Gluta-C$_{99}$YQTGYNQEIC$_{109+Amide}$ | 26 |
| mP4 | 125-40 | BDB-Y-CE$_{125}$FMKNNLKDNKKDKAR$_{140}$C$_{+Amide}$ | 32 |
| mP5 | 154-168 | $_{Acetyl+}$CN$_{154}$QEVKDLHKIVLPTP$_{168}$C-Y-BDB | 34 |
| mP6 | 176-188 | $_{Acetyl+}$D$_{176}$KCESQKEWLRTK$_{188}$C-Y-BDB | 33 |

The amino acids are annotated on the basis of Swissprot sequence P08505 (mIL-6)

Incomplete Freund's adjuvant (IFA) boosters are then given every 15 days, on D15, D30 and D45. The sera from mice on D54 are tested by ELISA with a 1/500$^{th}$ dilution of the serums on plates covered with murine IL-6 or human IL-6 in order to evaluate their cross-reactivity.

Figure 1:
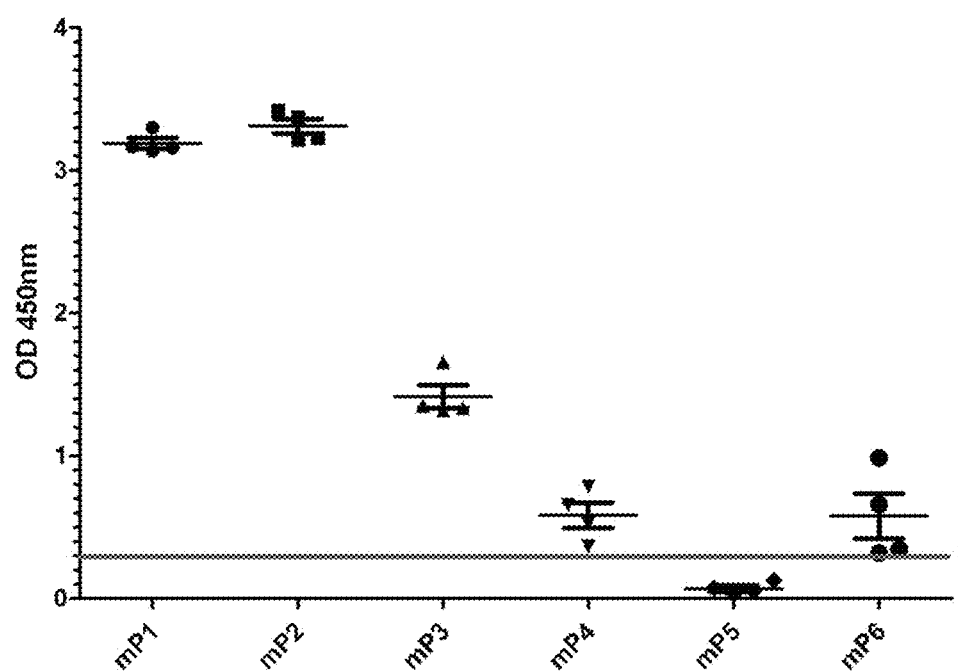
FIG. 1 represents the quantity of anti-mIL-6 antibodies present in serum diluted to $1/500^{th}$ from OF1 mice immunized with the peptides mP1, mP2, mP3, mP4, mP5 and mP6 measured by ELISA (y-axis, optical density (OD) at 450 nm). The horizontal line at 0.3 OD represents the significance threshold.

It is observed that all of the peptides tested with the exception of the peptide mP5 give rise to antibodies recognizing the murine cytokine (FIG. 1). Moreover, apart from the antibodies directed against the peptide mP2, the antibodies produced using the murine peptides show only a weak cross-reactivity with the human cytokine.

Example 2

Neutralization of the Biological Activity of the Murine IL-6 by Purified Antibodies Based on Serum from Rabbits Immunized with the Peptides Derived from Murine IL-6

The neutralizing ability of purified IgGs based on serum from rabbits immunized with the peptides mP1, mP2, mP3, mP4, mP5 and mP6 respectively, was tested in a murine IL-6 neutralization test. This test is based on the fact that murine B9 hybridomas proliferate in a dose-dependent manner in response to murine IL-6 (Brakenhoff et al. (1987) *J. Immunol.* 139:4116-21).

Description of the Experiment Carried Out:

Plating (D0): seed a flat-bottom 96-well plate, treated for cell culture with 5000 cells per well in 50 µL of neutralization medium. (RPMI 1640 without phenol red, 5% v/v Foetal Calf Serum (FCS), 2 mM L-Glutamine, 100 U/mL Penicillin/Streptomycin, 50 µm of β-Mercaptoethanol)

In parallel a so-called "pre-incubation" plate is produced with the desired concentration of murine IL-6, samples and commercial anti-mIL-6 antibodies used as positive control, all in a final volume of 100 µL of neutralization medium.

The pre-incubation plate is left at 37° C. for 2 hours. 50 µL per well is then transferred to the corresponding wells of the plate containing the cells, then the latter is incubated with 5% CO$_2$ at 37° C. for 96 hours.

Development (D4): Add 50 µL of a solution of XTT (for 2,3-bis-(2-methoxy-4-nitro-5-sulfophenyl)-2H-tetrazolium-5-carboxanilide)-0.5% electron coupling reagent to each well. Leave to incubate at 37° C. for 7 hours. Reading of the optical density on a spectrophotometer set at 450 nm.

It is observed that IgGs from the rabbits immunized with the peptides mP1, mP2, mP3, mP4 and mP6 neutralize the biological activity of murine IL-6 in a dose-dependent manner. On the other hand, IgGs from the rabbit immunized with the peptide mP5 do not neutralize the activity of murine IL-6.

Example 3

Clinical and Histological Protection after Vaccination Against a Peptide Derived from Murine IL-6 in a Murine Model of Chronic Colitis Induced by DSS Chronic colitis induced by Dextran Sodium Sulfate (DSS) is a well-known model of chronic inflammatory disease reproducing the main characteristics of the human diseases (Alex et al. (2009) *Inflamm. Bowel Dis.* 15:341-352).

Briefly, groups of 6 C57BL/6 mice (Charles River Laboratories, L'Arbresle, France) were formed. The mice were immunized 4 times (once with CFA and three times with IFA) every 15 days with different vaccine preparations. The mice were respectively immunized with PBS (DSS/PBS group), 50 µg per mouse of KLH (DSS/KLH group), and 100 µg per mouse of peptide mP1, mP2, mP3, mP4, mP5 and mP6 coupled with KLH (DSS/mIL-6 peptide group). A control H$_2$O group was also included. Four days after the first booster, colitis was induced by absorption of Dextran Sodium Sulfate (DSS) in water (2%) over 7 days followed by 7 days of water. Three DSS/water cycles were thus carried out, after which the mice received water until the end of the protocol. The clinical signs of the disease appear approximately on the fifth day after the start of treatment with DSS (D26 of the protocol). The development of the disease is measured from the start of the first DSS cycle up to the end of the protocol by a disease activity index (DAI) including weight loss, the presence of blood in the stools and the texture of the stools. The clinical scores are determined as follows: for the texture of the stools a score of 0 (hard stools) to 4 (diarrhoea), for the presence of blood in the stools a score of 0 (absence) to 4 (macroscopic blood), and weight loss a score of 0 (<1%) to 4 (>20%). Each mouse is thus assigned a clinical score with a maximum score of 12.

Figure 2:
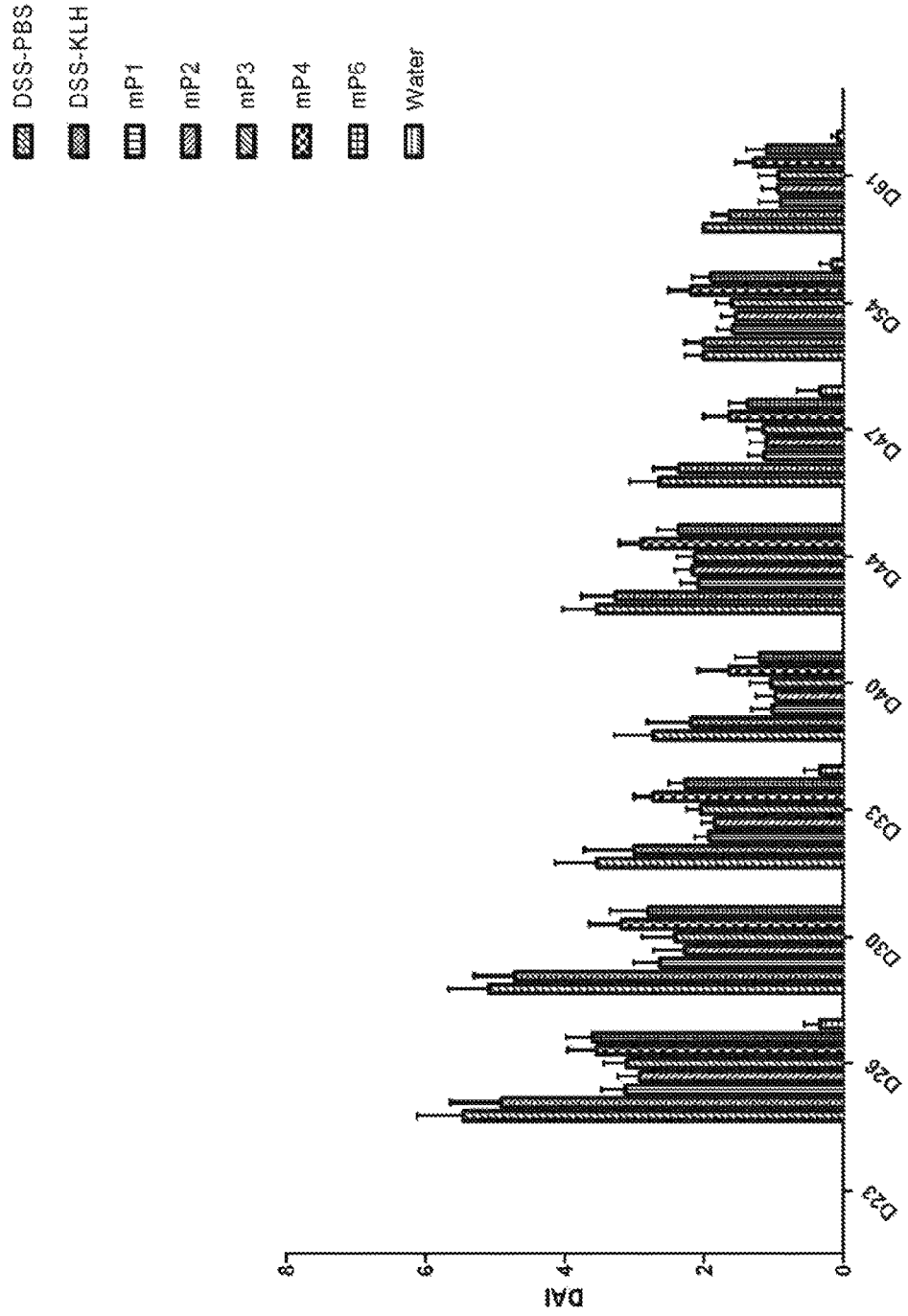
FIG. 2 represents the clinical score or disease activity index (DAI, y-axis) of untreated C57BL/6 mice (water) or mice treated with Dextran Sodium Sulfate (DSS) and vaccinated with the peptides mP1, mP2, mP3, mP4 and mP6, or with control vaccines without peptide and comprising buffer (PBS) or KLH carrier protein.

It is observed that the mice immunized with the peptides mP1, mP2, mP3, mP4 and mP6 have a significantly reduced disease activity index compared with the control groups (FIG. 2)

Then, on D67, the mice are killed by cervical dislocation. The histological sections from colon distal biopsies are scored blind, according to the severity of the inflammation (0: absence, 1: slight, 2: moderate, 3: severe), the extent of the inflammation (0: absence, 1: mucosal, 2: mucosal and sub-mucosal, 3: transmural), crypt damage (0: absence, 1:

one-third damaged, 2: 2/3 damaged, 3: only the surface of the epithelium intact, 4: total destruction of the crypts and epithelium). Each mouse is thus assigned a histological score with a maximum score of 10.

Figure 3:
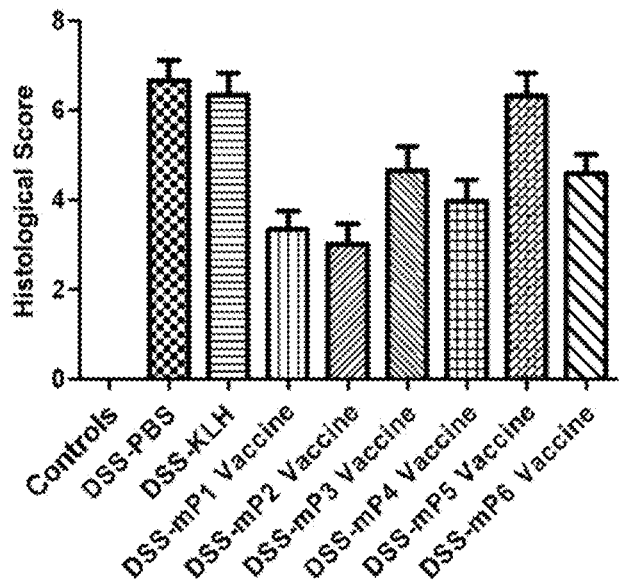
FIG. 3 represents the histological colitis score (y-axis) of untreated C57BL/6 mice (control) or mice treated with DSS and vaccinated with the peptides mP1, mP2, mP3, mP4 and mP6, or with control vaccines without peptide and comprising buffer (PBS) or KLH carrier protein.

It is observed that the mice immunized with the peptides mP1, mP2, mP3, mP4 and mP6 have a significantly reduced histological score compared with the control mice treated with PBS or KLH alone (FIG. 3).

Figure 4:
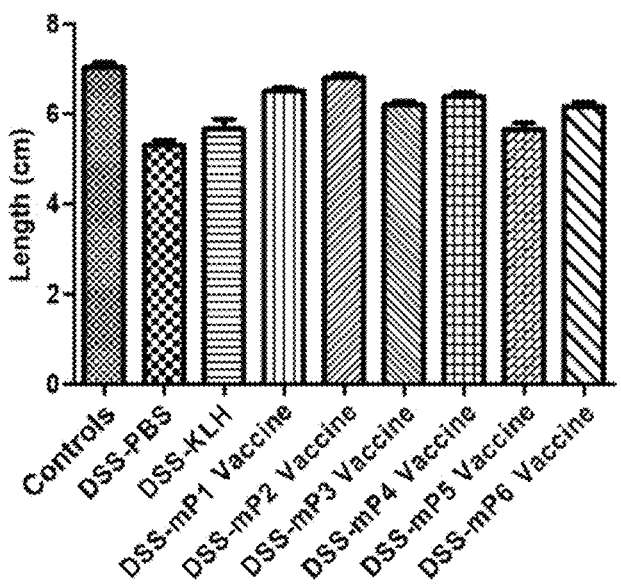
FIG. 4 represents the length of the colon (y-axis, in cm) of untreated C57BL/6 mice (control) or mice treated with DSS and vaccinated with the peptides mP1, mP2, mP3, mP4 and mP6, or with control vaccines without peptide and comprising buffer (PBS) or KLH carrier protein.

The absorption of DSS significantly reduces the length of the colon. Interestingly, the mice immunized with the peptides mP1, mP2, mP3, mP4 and mP6 exhibit a significantly less severe reduction of the colon than the control mice (FIG. 4). On the other hand, immunizations with KLH have no effect on the reduction in the length of the colon induced by DSS.

Example 4

Recognition of the Whole hIL-6 Cytokine by the Antibodies from Mice Immunized with Human IL-6 Peptides Similarly to Example 1, five peptides derived from human IL-6, hP1, hP2, hP3, hP4 and hP6 were coupled with KLH, four using the coupling agent BDB and one with glutaraldehyde (see Table 2). These peptides were cyclized using two cysteines (added or already present).

Figure 5:
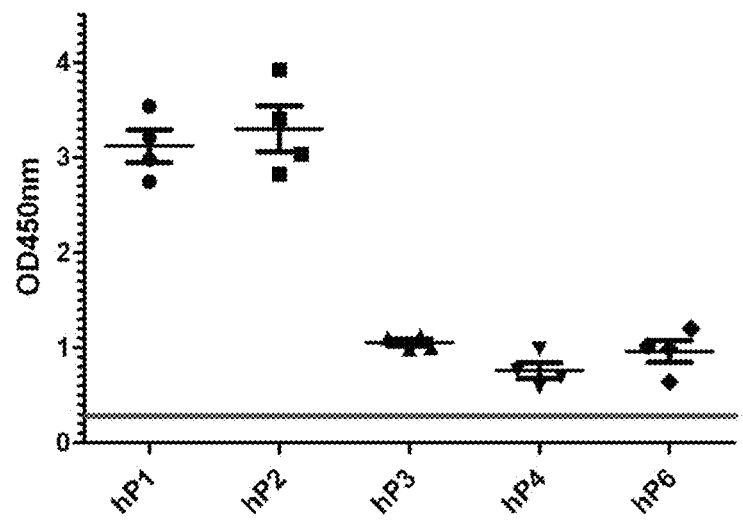
FIG. 5 represents the quantity of anti-hIL-6 antibodies present in serum diluted to $1/500^{th}$ from OF1 mice immunized with the peptides hP1, hP2, hP3, hP4 and hP6 measured by ELISA (y-axis, optical density (OD) at 450 nm). The horizontal line at 0.3 OD represents the significance threshold.

For each peptide, OF1 mice free from specific pathogenic organisms (n=4 per peptide) were immunized by intramuscular route with 100 µg of peptides derived from human IL-6 in CFA on D0. IFA boosters are then given every 15 days, on D15, D30 and D45. The serum is recovered after the boosters on D35 and D54 and tested by ELISA with a 1/500$^{th}$ dilution of the serums on plates covered with human IL-6 (FIG. 5).

gene encoding the human IL-6 receptor and the secreted embryonic alkaline phosphatase (SEAP) reporter gene (Supplier: Invivogen). The latter is then secreted in a dose-dependent manner in response to the human IL-6.

Briefly, the inventors proceeded as follows:

Plating (D0): seed a flat-bottom 96-well plate, treated for cell culture with 50,000 cells per well in 100 µL of neutralization medium. (DMEM 4.5 g/L glucose, 10% v/v FCS, 2 mM L-Glutamine, 100 U/mL Penicillin/Streptomycin, 100 µg/mL of Normocin).

In parallel a so-called "pre-incubation" plate is prepared with the desired concentration of human IL-6, rabbit antibodies and commercial anti-hIL-6 antibodies used as a positive control, all in a final volume of 200 µL of neutralization medium.

The pre-incubation plate is left at 37° C. for 2 hours. 100 µL per well is then transferred to the corresponding wells of the plate containing the cells, then the latter is incubated with 5% $CO_2$ at 37° C. for 24 hours.

Development (D1): Fill a flat-bottom 96-well plate with 180 µL per well of QUANTI-Blue (InVivoGen, CA, USA). Add 20 µL of supernatant from the plate treated with IL-6. Incubate with 5% $CO_2$ at 37° C. for 3 hours. Determine the quantity of secreted alkaline phosphatase using a spectrophotometer set at 620 nm.

It is observed that the IgGs from the rabbits immunized with the peptides hP1, hP2, hP3, hP4 and hP6 derived from human IL-6 neutralize the biological activity of the human IL-6 in a dose-dependent manner.

TABLE 2

Peptides derived from hIL-6 (underlined) used for the immunization

| Peptide | IL-6 region | Sequence | SEQ ID NO |
|---|---|---|---|
| hP1 | 63-78 | BDB-Y-$G_{63}$ISALRKETCNKSNM$C_{78+Amide}$ | 16 |
| hP2 | 78-94 | $_{Acetyl+}C_{78}$ESSKEALAENNLNLP$K_{94}$C-Y-BDB | 17 |
| hP3 | 101-111 | Gluta-$C_{10}$FQSGFNEET$C_{111+Amide}$ | 3 |
| hP4 | 127-141 | BDB-Y-C$E_{127}$FLQNRFESSEEQA$R_{141}C_{+Amide}$ | 18 |
| hP6 | 177-189 | $_{Acetyl+}T_{177}$KCQAQNQWLQD$M_{189}$C-Y-BDB | 19 |

The amino acids are annotated on the basis of Swissprot sequence P05231 (hIL-6)

Example 5

Neutralization of the Biological Activity of Human IL-6 by Purified Antibodies Based on Serum from Rabbits Immunized with Peptides Derived from Human IL-6

New Zealand rabbits free from specific pathogenic organisms (n=1 per peptide) were immunized with 100 µg of peptides hP1, hP2, hP3, hP4 and hP6 derived from human IL-6 by five immunizations with CFA/IFA on D0, D14, D28, D56 and J70. The neutralizing ability of the purified IgGs, derived from the serum of each rabbit, was tested in a human IL-6 neutralization test. This test is carried out on HEK293 cells (Human Embryonic Kidney cells) transfected with the Example 6

Production of Monoclonal Antibodies Targeting the Peptides hP2 and hP6, Recognizing the Human hIL-6 Cytokine and Neutralizing its Biological Activity 1) Production 2 groups of three SWISS mice are immunized against the 2 peptides hP2 and hP6 of human IL-6 (6 mice in all) with the following protocol: an initial immunization with 100 µg of peptide followed by 3 boosters on D20, D40, D60. The response titre is measured for each mouse and, for each peptide, the mouse exhibiting the best titre is used for the production of monoclonal antibodies.

For this, the hybridoma technique is used. Spleen B lymphocytes are purified, then fused with transformed myeloma cells in order to obtain immortal lines. These fused cells, called hybridomas, are maintained in selective medium, in the presence of aminopterin and hypoxanthine, so that the non-fused cells die: the myeloma cells because they have no thymidine kinase, and the B lymphocytes because they are not transformed. Only the fused cells can survive and the limiting dilution technique is then used to isolate clones producing only one species of antibody. At this stage, it is possible to test the antibodies produced in the supernatant by these clones by means of in vitro tests: ELISA against the recombinant cytokine and cytokine biological activity neutralization tests.

2) Screening

In a first step, for each peptide, 6 limiting-dilution plates are prepared. The dilutions are verified in each well by inverted-microscope analysis. A first screening is carried out by putting the supernatants into 12-well by 12-well groups and testing these groups by ELISA against the recombinant cytokine. The wells, the contents of which exhibit a positive signal, are tested individually: for the positive wells, a second limiting dilution is carried out on a plate.

For the second screening, the wells are also monitored by inverted microscopy. The supernatants are put into 8-well by 8-well groups, tested by ELISA, and for the positive pools, the responses of the individual wells are again analyzed by ELISA.

After the second screening step, it can reasonably be considered that the hybridomas present in the well originate from the same clone. These hybridomas are then cultured in bulk in order to produce larger quantities of antibodies.

Three hybridomas are selected for each peptide. For this, these cells are injected into the abdomens of mice where they proliferate in the form of ascites. The antibodies are then recovered by collecting the ascitic fluid from the peritoneal cavity and they are purified by using protein G affinity chromatography.

3) Neutralization of the Biological Activity of Human IL-6 by the Purified Anti-hIL-6 Monoclonal Antibodies On the basis of the human IL-6 biological activity neutralization test described in Example 5, the neutralizing ability of the monoclonal antibodies is evaluated at variable dilutions in order to study the dose-dependency of the human IL-6 biological activity neutralizing properties.

Example 7

Recognition of the Whole hIL-6 Cytokine by Antibodies Derived from the Serum from Mice Immunized with Variants of the Peptides hP1, hP2, hP3, hP4 and hP6

Five variants hP1', hP2', hP3', hP4' and hP6', derived from hP1, hP2, hP3, hP4, and hP6 respectively (see Table 3) were coupled to KLH, four using the coupling agent BDB and one with glutaraldehyde. These peptides were cyclized using two cysteines situated at the ends (added or already present in the native sequence).

TABLE 3

Peptides derived from hIL-6 used for the immunization

| Peptide | Sequence | SEQ ID NO | % identity |
|---|---|---|---|
| hP1 | BDB-Y-GISALRKETCNKSNM-C$_{+Amide}$ | 16 | 81.25% |
| hP1' | BDB-Y-GISAVRKDTCNKSQM-C$_{+Amide}$ | 20 | |
| hP2 | CESSKEALAENNLNLPK-C-Y-BDB | 17 | 84.21% |
| hP2' | CESSKDAIAENQLNLPK-C-Y-BDB | 21 | |
| hP3 | Gluta-CFQSGFNEETC$_{+Amide}$ | 3 | 81.81% |
| hP3' | Gluta-CFNSGFNEDTC$_{+Amide}$ | 10 | |
| hP4 | BDB-Y-C-EFLQNRFESSEEQAR-C$_{+Amide}$ | 18 | 82.35% |
| hP4' | BDB-Y-C-EFLQNRFDSSDENAR-C$_{+Amide}$ | 22 | |
| hP4 | BDB-Y-C-EFLQNRFESSEEQAR$_{+Amide}$ | 18 | 76.47% |
| hP4' | BDB-Y-C-DFLQNRFDSSDENAR$_{+Amide}$ | 57 | |
| hP6 | $_{Acetyl+}$TKCQAQNQWLQDM-C-Y-BDB | 19 | 80.00% |
| hP6' | $_{Acetyl+}$TKCQANQQWLQEM-C-Y-BDB | 23 | |

The variant parts are underlined

For each peptide, OF1 mice free from specific pathogenic organisms (n=4 per peptide) are immunized by intra-muscular route with 100 µg of variants hP1', hP2', hP3', hP4' and hP6' in CFA on D0. IFA boosters are then given every 15 days, on D15, D30 and D45. The serums from mice are tested on D54 by ELISA with a 1/500$^{th}$ dilution on plates covered with human IL-6.

Figure 6:
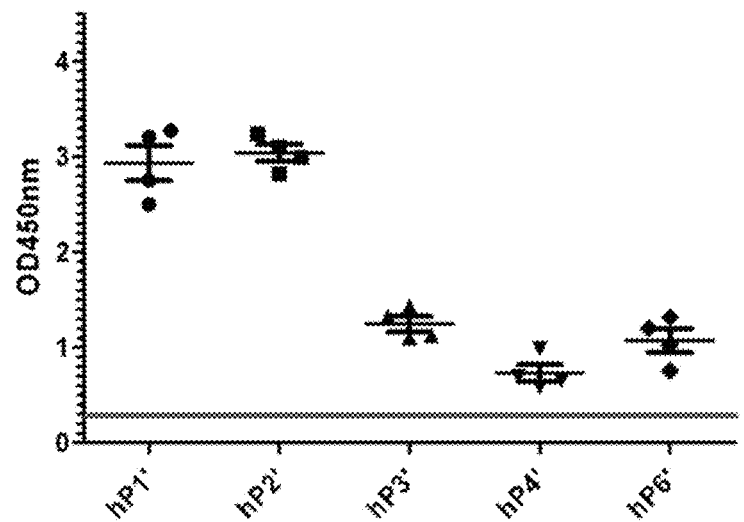
FIG. 6 represents the quantity of anti-hIL-6 antibodies present in the serum diluted to $1/500^{th}$ from OF1 mice immunized with the peptides hP1', hP2', hP3', hP4' and hP6' measured by ELISA (y-axis, optical density (OD) at 450 nm). The horizontal line at 0.3 OD represents the significance threshold.

It is observed that the peptide variants generate antibodies recognizing the human cytokine by ELISA (FIG. 6).

Finally, segments larger than 30 amino acids, containing hP1, hP2, hP3, hP4 and hP6 are also tested. These segments are also capable of generating human cytokine neutralizing antibodies.

Example 8

Human IL-6 Recognition (hIL-6) by Cynomolgus Monkey Sera, Immunized with a Peptide Derived from hIL-6

Four Cynomolgus monkeys were immunized intra-muscularly at day 0 with 150 µg of the cyclized hP2 peptide derived from hIL-6 previously described coupled to the protein carrier KLH, and then emulsified with the ISA51 adjuvant (Seppic).

Boosts were performed at d15, d30, d45 with an additional boost at d76. Blood samples were collected every two weeks until the end of the experiment (d120). These sera were tested in ELISA to evaluate the production of anti hIL-6 antibodies. A control group of four monkeys immunized with KLH only was used.

Figure 7:
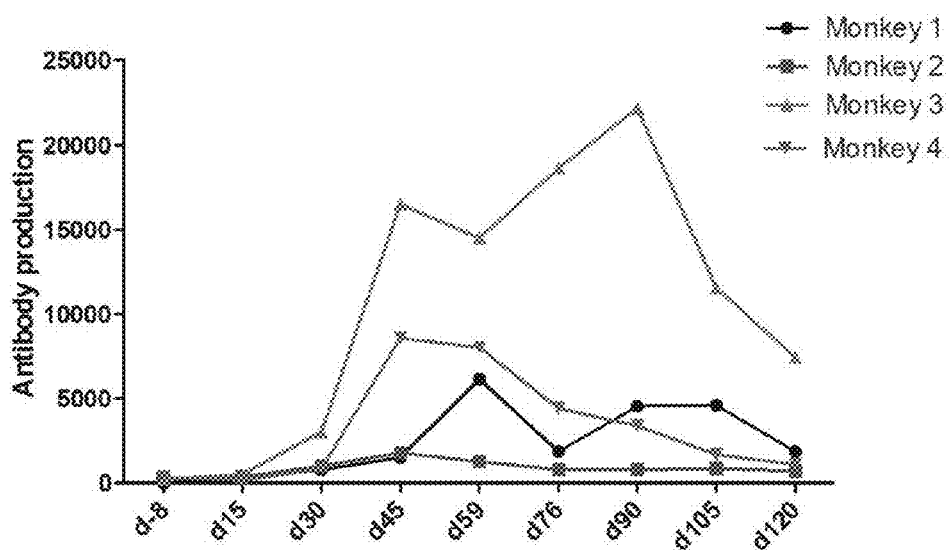
FIG. 7 represents the anti-hIL-6 antibody titer (vertical axis) of sera from monkeys immunized against hP2 as a function of time (horizontal axis, in days).

All the monkeys immunized with hP2, developed antibodies against hIL-6 from d30 with a kinetics showing a peak (in average at day 60) and a decrease of the antibody titers by the end of the experiment (FIG. 7).

The four control monkeys immunized with KLH only did not develop antibodies against hIL-6.

During this experiment, the inventors also evaluated the ability of the immunization against the peptide hP2 to modulate a delayed hypersensitivity against tetanus toxoid (TTx).

Briefly, the TTx vaccine (Sanofi-Pasteur, solution of 0.5 ml comprising 40 IU of Tetanus Toxoid and 0.6 mg of aluminium hydroxide) was administered intramuscularly at d59 in the thigh. Then an intradermic challenge was performed at d90 in two injection sites in the back of the monkey.

Clinical features of the cutaneous reaction were evaluated once a day for each animal before the challenge and then 24 h, 48 h and 72 h after the challenge. Each injection site was monitored for the incidence, grade and duration of three parameters (erythema, thickening, nodules) and a cumulative clinical score of delayed-type hypersensitivity (DTH) comprising these three parameters was established for each group.

Figure 8:
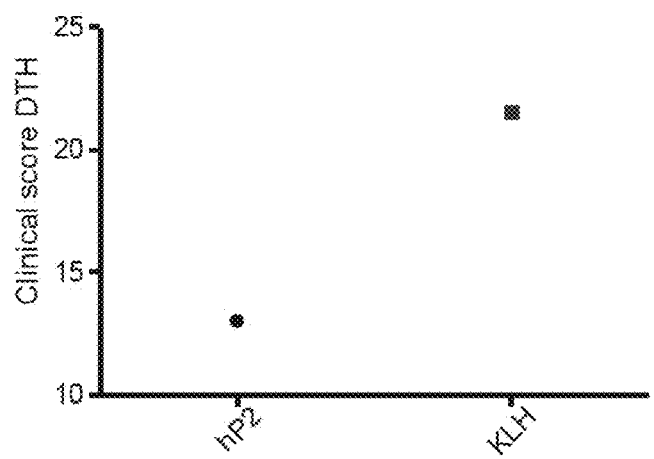
FIG. 8 represents the delayed-type hypersensitivity (DTH) clinical score (vertical axis, arbitrary units) of hP2-immunized monkeys and of control KLH-immunized monkeys.

Monkeys immunized with peptide hP2 showed a marked attenuation of the DTH response compared to the KLH group (FIG. 8), thus showing that the anti-IL6 antibodies induced by the immune reaction against the IL6 peptide immunogen are clinically effective.

Example 9

Clinical and Histological Protection after Vaccination with a Peptide Derived from Murine IL-6 in a Murine Model of Bleomycin Induced Systemic Sclerosis The murine model of bleomycin-induced systemic sclerosis is a well-known model of chronic inflammatory disease with main features being dermal thickness together with skin and pulmonary fibrosis due to excessive collagen production (Adamson & Bowden (1974) *Am. J. Pathol.* 77:185-197)

Briefly, three groups of DBA/2 mice (Janvier, France) immunized intramuscularly four times (once in complete Freund's adjuvant (CFA), and three times in incomplete Freund's adjuvant (IFA)) every 15 days with different vaccine preparations:

- 8 mice were immunized with 100 µg of the above-described cyclized mP2 peptide coupled to KLH (mP2-Bleo group) and were injected subcutaneously in the back with bleomycin
- 6 mice were immunized with 100 µg of mP2 (mP2-Nacl group) and were injected subcutaneously in the back with NaCl (Negative control group)
- 8 mice were group immunized with 200 µg of KLH alone (KLH-Bleo group) and were injected subcutaneously in the back with bleomycin. (Positive control group)

The inventors also used an additional control group composed of mice injected intraperitoneally with 100 µL (1 mg/mouse) of murine monoclonal anti IL-6 receptor antibody once a week (n=6).

The subcutaneous injections of 100 µL of bleomycin (0.5 mg/mL) were performed three days after the third boost and then every other day during three weeks in order to induce systemic sclerosis.

At day 54, the mice were killed. Sera samples were collected and the antibody production against mIL-6 was quantified by ELISA. Furthermore, skin biopsies were performed to evaluate the OH-proline production, indicative of collagen production, and histological sections from the back were also performed to evaluate dermal thickness.

Figure 9:
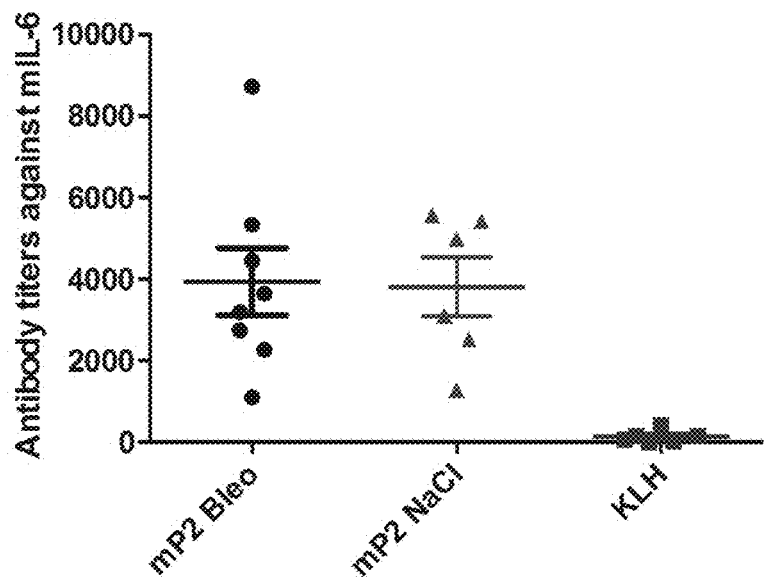
FIG. 9 represents the anti-mIL-6 antibody titer (vertical axis) of mice immunized against mP2 or KLH and having received injections of bleomycin (Bleo) or of NaCl.

All mice developed antibodies against mIL-6 after immunization against mP2 while the mice immunized against KLH only did not (FIG. 9).

The collagen content was measured in the skin biopsy from each mouse by assaying hydroxyproline (OH-proline) content. OH-proline represents about 13% of collagen amino acids and is measured to evaluate collagen production. Briefly, an acid hydrolysis is performed on two biopsy punch, then OH-proline oxidation is realised which leads to pyloric derivatives with pink coloration as described by Woessner (1961) *Arch. Biochem. Biophys.* 93:440-447. The absorbance is read at 560 nm.

Figure 10:
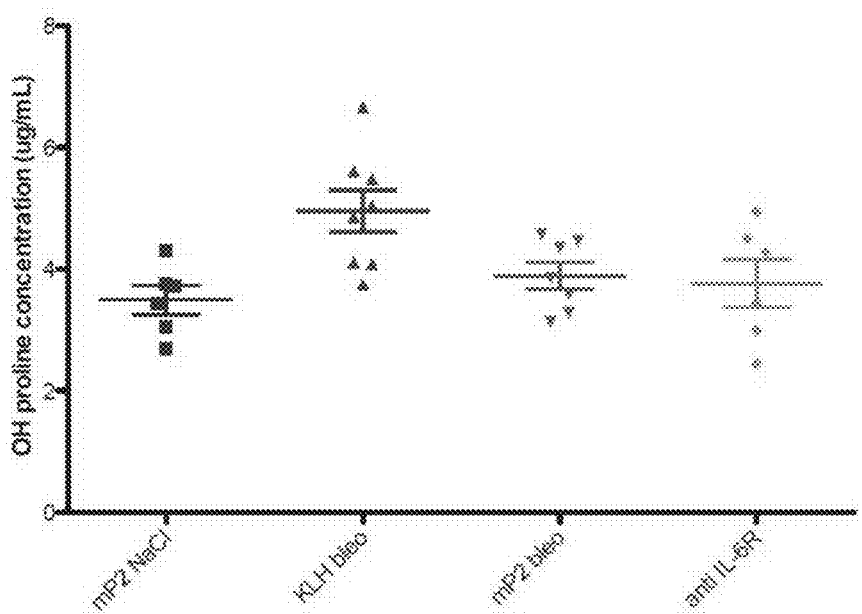
FIG. 10 represents hydroxyproline (OH proline) concentration (vertical axis, in µg/ml) in skin biopsies of mice immunized with mP2 or KLH or having received an anti-IL-6 receptor antibody (anti IL-6R) and injected with either bleomycin (bleo) or NaCl.

The negative control group immunized with mP2 and injected subcutaneously with NaCl did not develop skin fibrosis whereas the positive control group, mice immunized with KLH only and injected with bleomycin, developed fibrosis. Furthermore the group immunized with mP2 and injected subcutaneously with bleomycin was protected from the development of fibrosis with the same efficacy as the group receiving the anti IL-6 receptor antibody (FIG. 10). Dermal thickness from histological sections was then measured in a blind way by two independent experts.

Figure 11:
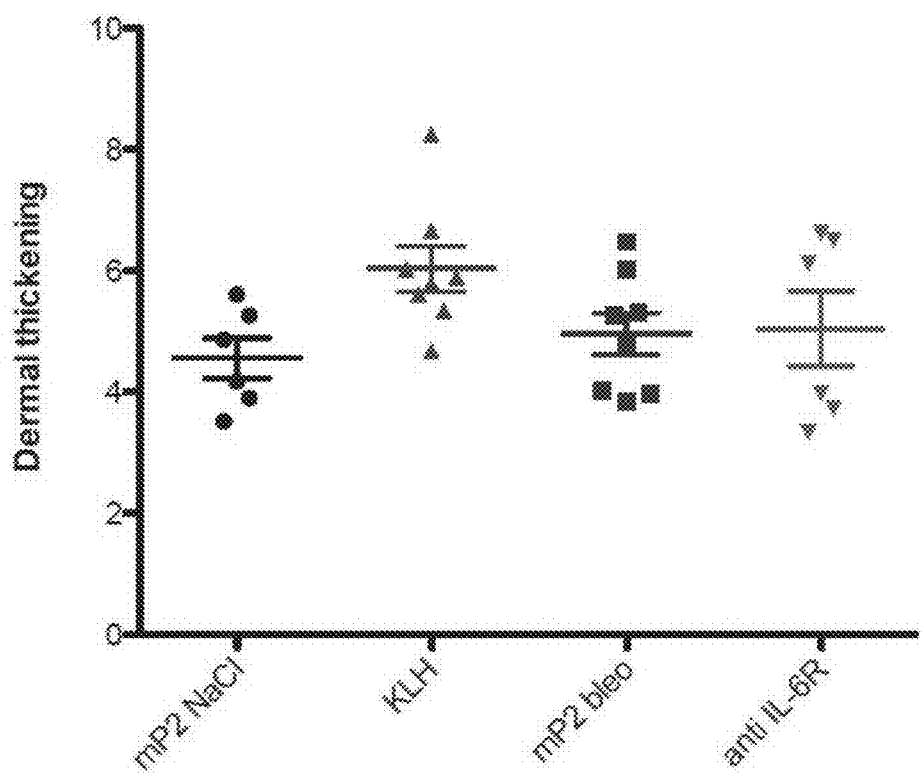
FIG. 11 represents dermal thickening (vertical axis, in arbitrary units) from histological sections of mice immunized with mP2 or KLH or having received an anti-IL-6 receptor antibody (anti IL-6R) and injected with either bleomycin (bleo) or NaCl.

Mice immunized against mP2 had a lower dermal thickening than mice immunized with KLH only, and it was identical with the dermal thickness observed for the group receiving anti mIL-6 receptor (FIG. 11).

In conclusion, immunization against the mP2 peptide protected mice from fibrosis and dermal thickening in the murine model of bleomycin-induced systemic sclerosis.

The invention claimed is:

1. A method for reducing symptoms of an arthritic disease, comprising administering to an individual in need thereof a therapeutically effective amount of at least one cyclized polypeptide with a length equal to 25 amino acids or less, wherein the at least one cyclized polypeptide comprises, or consists of, a sequence selected from the group consisting of SEQ ID NO: 2, 3, 17, 18 and 19, and a variant sequence thereof having at least 90% sequence identity with the sequence of SEQ ID NO: 2, 3, 17, 18 or 19 and elicits a protective anti-human IL-6 immune reaction.

2. The method of claim 1, wherein the arthritic disease is selected from the group consisting of rheumatoid arthritis, juvenile rheumatoid arthritis, psoriatic arthritis, arthrosis, refractory rheumatoid arthritis, chronic non-rheumatoid arthritis and ankylosing spondylitis.

3. The method of claim 1, wherein the cyclized polypeptide elicits anti-human IL-6 antibodies.

4. The method of claim 1, wherein the cyclized polypeptide is bound to a carrier macromolecule.

5. The method of claim 1, wherein the cyclized polypeptide comprises, or consists of, a sequence selected from the group consisting of SEQ ID NO:2, SEQ ID NO:17, and a variant thereof having at least 90% sequence identity with the sequence of SEQ ID NO:2 or SEQ ID NO:17.

* * * * *